(12) United States Patent
Dant et al.

(10) Patent No.: US 8,672,978 B2
(45) Date of Patent: Mar. 18, 2014

(54) TRANSVERSE CONNECTOR

(75) Inventors: Jack Dant, St. Paul, MN (US); Christopher Bargsten, New Brighton, MN (US); Peter Schulte, Richmond, MN (US); Hugh Hestad, Edina, MN (US); Brad Kessler, Bloomington, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 165 days.

(21) Appl. No.: 13/041,031

(22) Filed: Mar. 4, 2011

(65) Prior Publication Data

US 2012/0226316 A1    Sep. 6, 2012

(51) Int. Cl.
    *A61B 17/70*    (2006.01)
(52) U.S. Cl.
    USPC ............................ 606/250; 606/253; 606/264
(58) Field of Classification Search
    USPC .................. 606/250–278, 288–294, 305–308
    See application file for complete search history.

(56) References Cited

U.S. PATENT DOCUMENTS

| | | | |
|---|---|---|---|
| 4,484,570 A | 11/1984 | Sutter et al. | |
| 5,092,867 A | 3/1992 | Harms et al. | |
| 5,261,907 A | 11/1993 | Vignaud et al. | |
| 5,261,910 A | 11/1993 | Warden et al. | |
| 5,269,784 A | 12/1993 | Mast | |
| 5,304,179 A | 4/1994 | Wagner | |
| 5,397,363 A | 3/1995 | Gelbard | |
| 5,403,316 A | 4/1995 | Ashman | |
| 5,498,263 A | 3/1996 | DiNello et al. | |
| 5,501,684 A | 3/1996 | Schlapfer et al. | |
| 5,527,314 A | 6/1996 | Brumfield et al. | |
| 5,573,548 A * | 11/1996 | Nazre et al. | 606/232 |
| 5,584,887 A | 12/1996 | Kambin | |
| 5,601,554 A | 2/1997 | Howland et al. | |
| 5,693,053 A | 12/1997 | Estes | |
| 5,709,686 A | 1/1998 | Talos et al. | |
| 5,713,900 A | 2/1998 | Benzel et al. | |
| 5,735,853 A | 4/1998 | Olerud | |
| 5,800,435 A | 9/1998 | Errico et al. | |
| 5,947,966 A | 9/1999 | Drewry et al. | |
| 5,954,722 A | 9/1999 | Bono | |
| 5,989,251 A | 11/1999 | Nichols | |
| 6,050,997 A | 4/2000 | Mullane | |
| 6,077,262 A | 6/2000 | Schlapfer et al. | |
| 6,096,039 A | 8/2000 | Stoltenberg et al. | |

(Continued)

FOREIGN PATENT DOCUMENTS

WO    2008039777 A3    9/2008

*Primary Examiner* — Jan Christopher Merene
(74) *Attorney, Agent, or Firm* — Seager, Tufte & Wickhem, LLC

(57) ABSTRACT

A transverse connector for coupling between first and second vertebral anchors of a spinal stabilization system. The transverse connector includes a first coupling assembly proximate a first end, a second coupling assembly proximate a second end, a first fastener having external threading configured to threadably engage an internal threaded portion of a housing of the first vertebral anchor, and a second fastener having external threading configured to threadably engage an internal threaded portion of a housing of the second vertebral anchor. Each of the first and second fasteners includes a spherical upper surface, such as a spherically concave upper surface. A spherical surface of each of the first and second coupling assemblies mates with the spherical upper surface of the respective fastener to provide multi-axial rotation of the transverse connector relative to the housings to permit a desired orientation of the transverse connector.

13 Claims, 19 Drawing Sheets

(56) References Cited

U.S. PATENT DOCUMENTS

| | | | |
|---|---|---|---|
| 6,235,033 B1 | 5/2001 | Brace | |
| 6,238,396 B1 | 5/2001 | Lombardo | |
| 6,283,967 B1 | 9/2001 | Troxell et al. | |
| 6,454,769 B2 | 9/2002 | Wagner et al. | |
| 6,485,491 B1 * | 11/2002 | Farris et al. | 606/250 |
| 6,530,929 B1 | 3/2003 | Justis et al. | |
| 6,616,668 B2 | 9/2003 | Altarac et al. | |
| 6,641,583 B2 | 11/2003 | Shluzas et al. | |
| 6,669,701 B2 | 12/2003 | Steiner et al. | |
| 6,679,883 B2 | 1/2004 | Hawkes et al. | |
| 6,682,529 B2 | 1/2004 | Stahurski | |
| 6,689,133 B2 | 2/2004 | Morrison et al. | |
| 6,719,759 B2 | 4/2004 | Wagner et al. | |
| 6,736,817 B2 | 5/2004 | Troxell et al. | |
| 6,761,721 B2 | 7/2004 | Burgess et al. | |
| 6,945,972 B2 | 9/2005 | Frigg | |
| 7,048,739 B2 * | 5/2006 | Konieczynski et al. | 606/288 |
| 7,118,303 B2 | 10/2006 | Doubler et al. | |
| 7,137,986 B2 | 11/2006 | Troxell et al. | |
| 7,160,301 B2 | 1/2007 | Cordaro | |
| 7,276,069 B2 | 10/2007 | Biedermann et al. | |
| 7,334,961 B2 | 2/2008 | Doubler et al. | |
| 7,354,441 B2 | 4/2008 | Frigg | |
| 7,491,221 B2 | 2/2009 | David | |
| 7,569,070 B2 | 8/2009 | Suzuki et al. | |
| 7,615,068 B2 | 11/2009 | Timm et al. | |
| 7,635,379 B2 | 12/2009 | Callahan et al. | |
| 7,645,294 B2 | 1/2010 | Kalfas et al. | |
| 7,678,136 B2 | 3/2010 | Doubler et al. | |
| 7,717,939 B2 | 5/2010 | Ludwig et al. | |
| 7,722,648 B2 | 5/2010 | Drewry et al. | |
| 7,744,635 B2 | 6/2010 | Sweeney et al. | |
| 7,776,076 B2 | 8/2010 | Grady, Jr. et al. | |
| 7,780,704 B2 | 8/2010 | Markworth et al. | |
| 8,211,108 B2 * | 7/2012 | Matityahu | 606/64 |
| 8,246,665 B2 * | 8/2012 | Butler et al. | 606/308 |
| 8,267,978 B2 * | 9/2012 | Lindemann et al. | 606/305 |
| 8,480,716 B2 * | 7/2013 | Perrow et al. | 606/286 |
| 2002/0138077 A1 | 9/2002 | Ferree | |
| 2002/0169448 A1 | 11/2002 | Vanacker | |
| 2003/0208204 A1 * | 11/2003 | Bailey et al. | 606/69 |
| 2005/0192578 A1 | 9/2005 | Horst | |
| 2005/0251141 A1 * | 11/2005 | Frigg et al. | 606/61 |
| 2006/0009773 A1 | 1/2006 | Jackson | 606/73 |
| 2006/0149265 A1 * | 7/2006 | James et al. | 606/73 |
| 2006/0206208 A1 * | 9/2006 | Michelson | 623/17.11 |
| 2006/0264936 A1 * | 11/2006 | Partin et al. | 606/61 |
| 2007/0270809 A1 | 11/2007 | Drewry et al. | |
| 2008/0021464 A1 | 1/2008 | Morin et al. | |
| 2008/0269751 A1 * | 10/2008 | Matityahu | 606/64 |
| 2009/0043339 A1 | 2/2009 | Tepper et al. | |
| 2009/0088807 A1 | 4/2009 | Castaneda et al. | |
| 2009/0228046 A1 | 9/2009 | Garamszegi | |
| 2009/0254123 A1 | 10/2009 | Pafford et al. | |
| 2010/0036420 A1 | 2/2010 | Kalfas et al. | |
| 2010/0057131 A1 | 3/2010 | Ely et al. | |
| 2010/0087867 A1 | 4/2010 | Klein et al. | |
| 2010/0094345 A1 | 4/2010 | Saidha et al. | |
| 2010/0160981 A1 | 6/2010 | Butler et al. | |
| 2010/0211116 A1 * | 8/2010 | Suh et al. | 606/305 |

* cited by examiner

TRANSVERSE CONNECTOR

TECHNICAL FIELD

The disclosure is directed to transverse connectors for use in a spinal stabilization system. More particularly, the disclosure is directed to transverse connectors which may be attached between vertebral anchors in a spinal stabilization system.

BACKGROUND

The spinal column is a highly complex system of bones and connective tissues that provides support for the body and protects the delicate spinal cord and nerves. The spinal column includes a series of vertebrae stacked one on top of the other. Each vertebra includes a vertebral body including an inner or central portion of relatively weak cancellous bone and an outer portion of relatively strong cortical bone. An intervertebral disc is situated between each vertebral body to cushion and dampen compressive forces experienced by the spinal column. A vertebral canal, called the foramen, containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal curvature and twisting of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

In some instances, a spinal stabilization system may be installed on a segment of the spinal column to stabilize a portion of the spinal column to treat a spinal disorder. One particular spinal stabilization technique includes immobilizing portions of the spine of a patient by using elongate members such as relatively rigid orthopedic spinal rods that run generally parallel to the spine on opposite sides of the spinous processes. Another technique utilizes less rigid elongate members to provide a more dynamic stabilization of the affected regions of the spine. One example of such a spinal stabilization system is the Dynesys® system available from, Zimmer Spine, Inc., of Minneapolis, Minn.

Installation of such systems may be accomplished, for example, by accessing the spine posterially and fastening hooks, bone screws, or other types of vertebral anchors to the pedicles or other bony structures of the appropriate vertebrae. The vertebral anchors may be generally placed in a quantity of two per vertebra, one on either side of the spinous processes, and serve as anchor points for the elongate members.

It may be desirable in some circumstances to provide a cross connector, such as a transverse connector, to bridge across the spinal column from a first assembly of vertebral anchors and associated elongate member to a second assembly of vertebral anchors and associated elongate member of the spinal stabilization system to provide additional stability to the spinal stabilization system. Accordingly, there exists a need to provide alternative transverse connector assemblies which may be coupled between first and second vertebral anchors of a spinal stabilization system.

SUMMARY

The disclosure is directed to several alternative designs, materials and methods of manufacturing medical device structures and assemblies.

Accordingly, one illustrative embodiment is a transverse connector for coupling between first and second vertebral anchors of a spinal stabilization system. The transverse connector includes a first coupling assembly proximate a first end of the transverse connector and a second coupling assembly proximate a second end of the transverse connector. The transverse connector also includes a first fastener having external threading configured to threadably engage an internal threaded portion of a housing of the first vertebral anchor and a second fastener having external threading configured to threadably engage an internal threaded portion of a housing of the second vertebral anchor. Each of the first and second fasteners includes a spherical upper surface. A spherical surface of the first coupling assembly mates with the spherical upper surface of the first fastener and a spherical surface of the second coupling assembly mates with the spherical upper surface of the second fastener.

Another illustrative embodiment is a spinal stabilization system including first, second, third and fourth vertebral anchors, each including a housing and a bone engagement portion extending from the housing, with a first elongate member extending between the first and third vertebral anchors and a second elongate member extending between the second and fourth vertebral anchors. The spinal stabilization system further includes a first fastener securing the first elongate member in a channel of the housing of the first vertebral anchor and a second fastener securing the second elongate member in a channel of the housing of the second vertebral anchor. Each of the first and second fasteners includes a spherical upper portion having a spherically convex surface and a threaded lower portion threadably engaging the housing of the respective vertebral anchor. The spinal stabilization system also includes a transverse connector including a first coupling housing proximate a first end of the transverse connector and a second coupling housing proximate a second end of the transverse connector. The first coupling housing includes an aperture therethrough for receiving the spherical upper portion of the first fastener and the second coupling housing includes an aperture therethrough for receiving the spherical upper portion of the second fastener. Each aperture has a concave annular sidewall configured to mate with the spherically convex surface of the spherical upper portion of the respective fastener to allow rotational movement therebetween.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
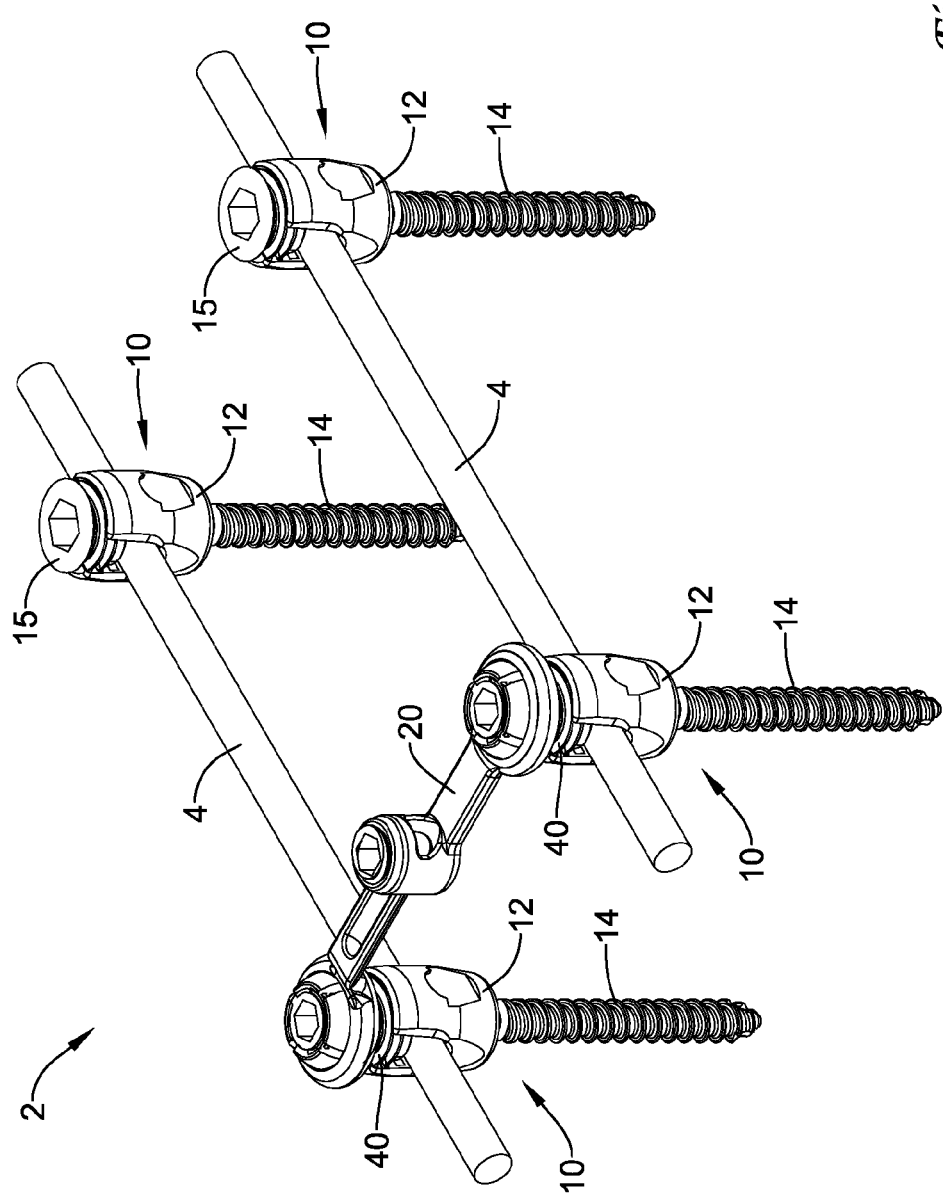
FIG. 1 is a perspective view of an exemplary spinal stabilization system including a transverse connector extending between vertebral anchors.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the drawings, an exemplary spinal stabilization system 2 for stabilizing a portion of a spinal column, such as one or more spinal segments of a spinal column, is illustrated in FIG. 1. As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. The spinal stabilization system 2 may provide support to the spinal segment subsequent bone fusion, may help preserve the facet joints between adjacent vertebrae by providing facet offloading and/or may stabilize or reverse neural foraminal narrowing of the spinal column, in some instances.

In some embodiments, the spinal stabilization system 2 may be used to treat discogenic low back pain, degenerative spinal stenosis, disc herniations, facet syndrome, posterior element instability, adjacent level syndrome associated with spinal fusion, and/or other maladies associated with the spinal column.

The spinal stabilization system 2 may include one or more or a plurality of vertebral anchors 10. Although the vertebral anchors 10 are depicted as threaded vertebral fasteners (e.g., pedicle screws, bone screws), in some embodiments the vertebral anchors 10 may be vertebral hooks (e.g., laminar hooks) or other types of fastening members for attachment to a bony structure such as a vertebra of the spinal column. Each of the vertebral anchors 10 may be configured to be secured to a vertebra of a spinal column.

The spinal stabilization system 2 may be used in any desired region of the spinal column, such as the cervical, thoracic, thoracolumbar, and lumbar regions. The vertebral stabilization system 2 may be installed multi-laterally on opposite sides of the sagittal plane of the spinal column, with the first and third vertebral anchors 10a, 10c and the first elongate member 4 positioned on one lateral side of the sagittal plane and the second and fourth vertebral anchors 10b, 10d and the second elongate member 4 positioned on the other lateral side (i.e., contra-lateral side) of the sagittal plane. For instance, the first vertebral anchor 10a and the second vertebral anchor 10b may be secured to a first vertebra on contra-lateral sides of the sagittal plane, while the third vertebral anchor 10c and the fourth vertebral anchor 10d may be secured to a second vertebra on contra-lateral sides of the sagittal plane. Additional vertebral anchors 10 may be secured to additional vertebrae as desired.

The vertebral anchor 10 may include a housing 12 and a bone engagement portion, such as a bone screw 14 extending from the housing 12 along a longitudinal axis of the vertebral anchor 10. In some embodiments, the vertebral anchor 10 may be a monoaxial screw in which the housing 12 is stationary relative to the bone screw 14, while in other embodiments the vertebral anchor 10 may be a polyaxial screw in which the housing 12 is actuatable (e.g., pivotable) relative to the bone screw 14. In some embodiments, the bone screw 14 may be configured to be installed into a bony region of a vertebra of the spinal column. For example, the bone screw 14 may be installed into a pedicle of a vertebra, or other region of a vertebra. In some embodiments, the bone screw 14 may include helical threads configured to be screwed into a pedicle of a vertebra, or other bony region of a vertebra.

The housing 12 may include a base portion and first and second legs 8 extending from the base portion and defining a channel 6, such as a U-shaped channel, therebetween extending into the housing 12 from an upper extent of the housing 12 opposite the bone screw 14. In some embodiments each of the first and second legs 8 may include a threaded portion for threadedly engaging a threaded portion of a fastener. In other embodiments, the first and second legs 8 may include other engagement features for engaging with a securing member positioned in the housing 12 between the first and second legs 8.

The spinal stabilization system 2 may also include one or more, or a plurality of elongate stabilization members 4, such as elongate rods, extending between vertebral anchors 10 of the spinal stabilization system 2. As an illustrative example, the spinal stabilization system 2 shown in FIG. 1 includes a first elongate member 4 extending between and secured to the first vertebral anchor 10a and the third vertebral anchor 10c, and a second elongate member 4 extending between and secured to the second vertebral anchor 10b and the fourth vertebral anchor 10d.

The elongate members 4 may be secured in the channels 6 of the housings 12 of the vertebral anchors 10 using threaded fasteners or other securement members. For instance, threaded set screws 15 may be threadably engaged with the threaded portions of the legs 8 of the housings 12 of the third and fourth vertebral anchors 10c, 10d and press against the elongate member 4 to secure the elongate members 4 in the channels 6.

The spinal stabilization system 2 may also include a transverse connector 20 which may be positioned generally perpendicular to the elongate members 4 to provide additional stability to the spinal stabilization system 2 in some instances. The transverse connector 20 may be configured to be coupled to the housings 12 of contra-laterally positioned vertebral anchors 10. For example, the transverse connector 20 may be coupled between the first and second vertebral anchors 10a, 10b in an orientation generally perpendicular to the elongate members 4. The transverse connector 20 may include fasteners 40 having external threading configured to threadably engage an internal threaded portion of the housing 12 between the legs 8 of a vertebral anchor 10. The fasteners 40 may press against the elongate member 4 to secure the elongate members 4 in the channels 6 of the housings 12 of the first and second vertebral anchors 10a, 10b.

In some instances, it may be desirable to install the transverse connector 20 between vertebral anchors 10 on a single side of the spinal column, thus the transverse connector 20 may extend generally parallel to the elongate member 4 coupled between adjacent vertebral anchors 10. For instance, the elongate member 4 may be coupled to the first and third vertebral anchors 10a, 10c on a single side of the sagittal plane of the spinal column, with the transverse connector 20 also secured to and extending between the first and third vertebral anchors 10a, 10c on the same side of the sagittal plane of the spinal column. Thus, the transverse connector 20 may extend parallel to the elongate member 4 in a vertical direction generally parallel with the longitudinal axis of the spinal column.

Figure 2:
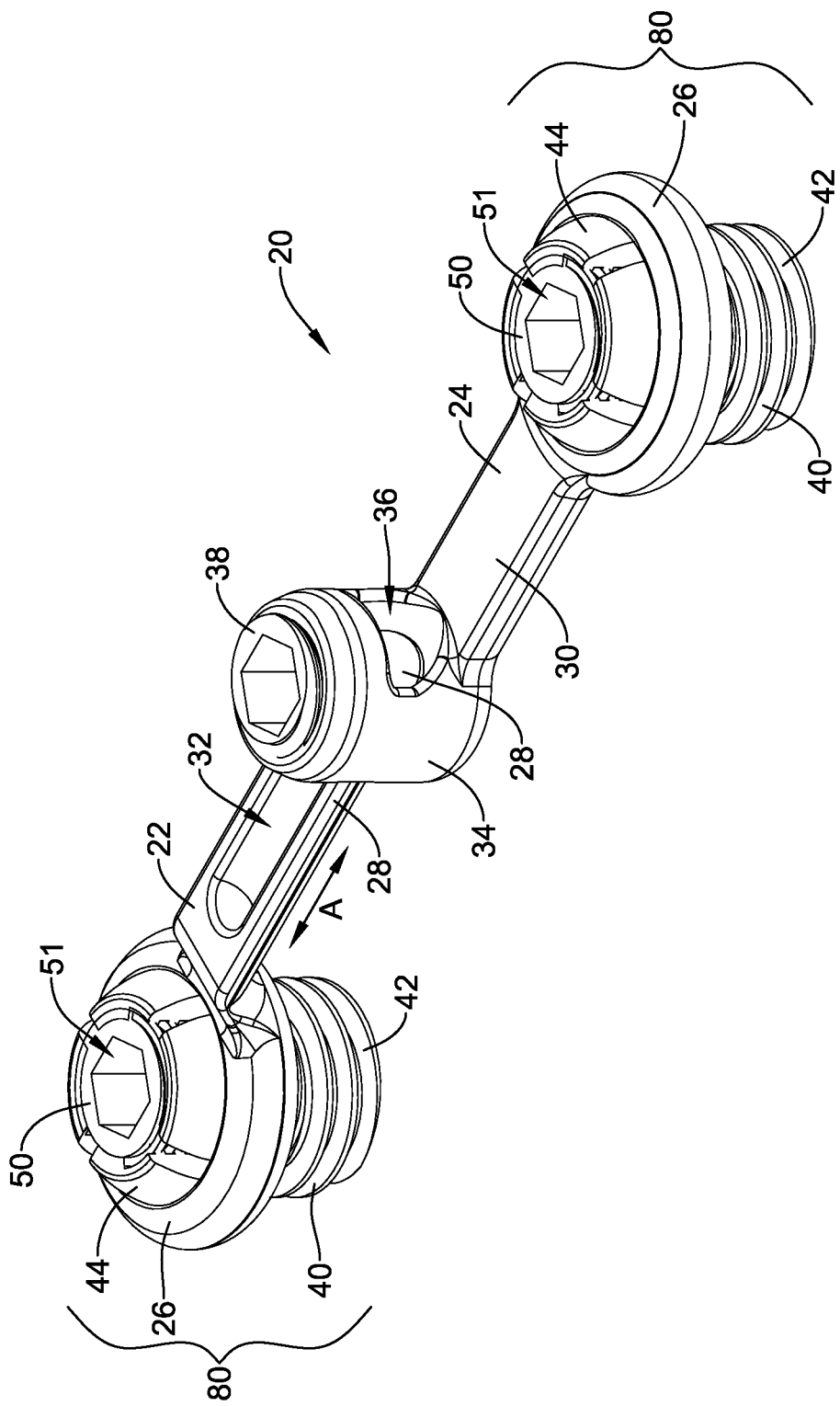
FIG. 2 is a perspective view of the transverse connector shown in FIG. 1.

Additional features and components of the transverse connector 20 are further illustrated in FIGS. 2-7. As shown in FIG. 2, the transverse connector 20 may include a first connector member 22 and a second connector member 24 coupled together. For instance, the first connector member 22, which may be considered a male connector member, may include a coupling housing 26 and an elongate extension 28 extending from the coupling housing 26. Furthermore, the second connector member 24, which may be considered a female connector member, may include a coupling housing 26 and an elongate extension 30 extending from the coupling housing 26. The elongate extension 30 may include a receiver 34 with an opening 36 therethrough for receiving the elongate extension 28 of the first connector member 22.

The transverse connector 20 may be configured such that the first connector member 22 may be moved in multiple degrees of freedom relative to the second connector member 24. For example, the first connector member 22 may translate along a longitudinal axis (see arrow A, FIG. 2) and rotate about the longitudinal axis (see Arrow B, FIG. 7) relative to the second connector member 24, in some instances. In some embodiments, the transverse connector 20 may include additional degrees of freedom, such as pivot about an axis transverse to the longitudinal axis. When the first connector member 22 is positioned at a desired orientation relative to the second connector member 24, the locking screw 38, threadably engaged in a threaded bore of the receiver 34, may be rotated into engagement against the elongate extension 28 of the first connector member 22 to apply a clamping force between the first connector member 22 and the second connector member 24 to thereby prevent further movement therebetween.

Figure 3:
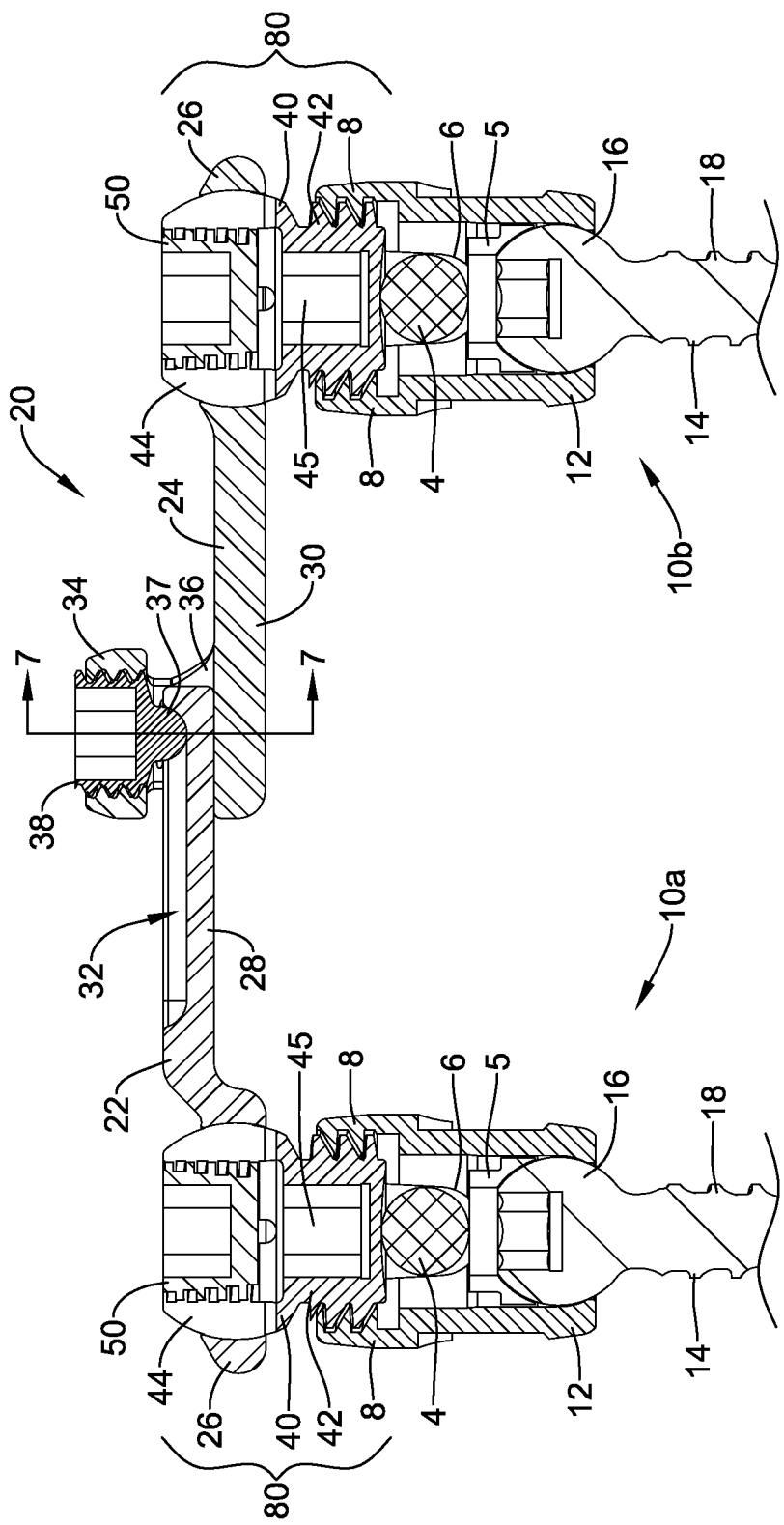
FIG. 3 is a cross-sectional view of the transverse connector of FIG. 1.
Figure 7:
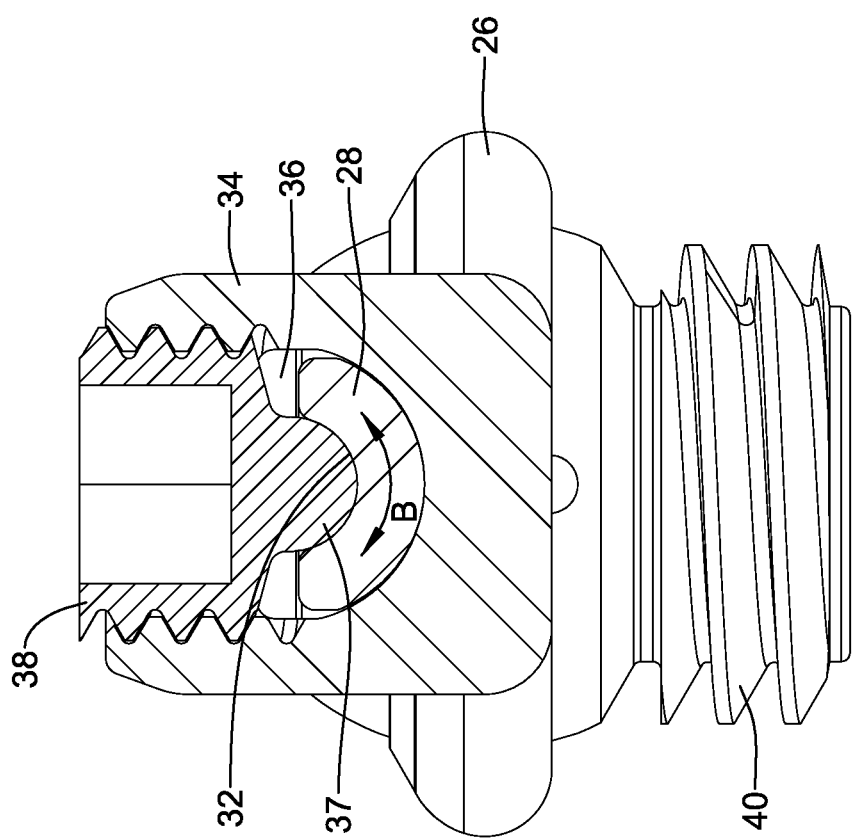
FIG. 7 is a cross-sectional view of the transverse connector of FIG. 2 taken through line 7-7.

Referring to FIG. 7, the locking screw 38 may include a protuberance 37, which may be a spherical protuberance, extending into an elongate recess 32 of the elongate extension 28 of the first connector member 22. The arcuate lower surface of the protuberance 37, the arcuate surface of the recess 32 and the arcuate lower wall of the opening 36 may share a common center of curvature. Thus, as can be seen by the arrow B, the elongate extension 28 of the first connector member 22 may rotate about the common center of curvature relative to the second connector member 24 to adjust the orientation of the first connector member 22 relative to the second connector member 24. As shown in FIG. 3, the recess 32 may include end surfaces which limit the longitudinal travel of the protuberance 37 in the recess 32, and thus prevent decoupling of the first connector member 22 from the second connector member 24.

The transverse connector 20 may include coupling assemblies 80 configured to secure the transverse connector 20 to the housings 12 of vertebral anchors 10. As shown in FIG. 3, a first coupling assembly 80 proximate the first end of the transverse connector 20 may couple the transverse connector 20 to a first vertebral anchor 10 and a second coupling assembly 80 proximate the second end of the transverse connector 20 may couple the transverse connector 20 to a second vertebral anchor 10.

Figure 4:
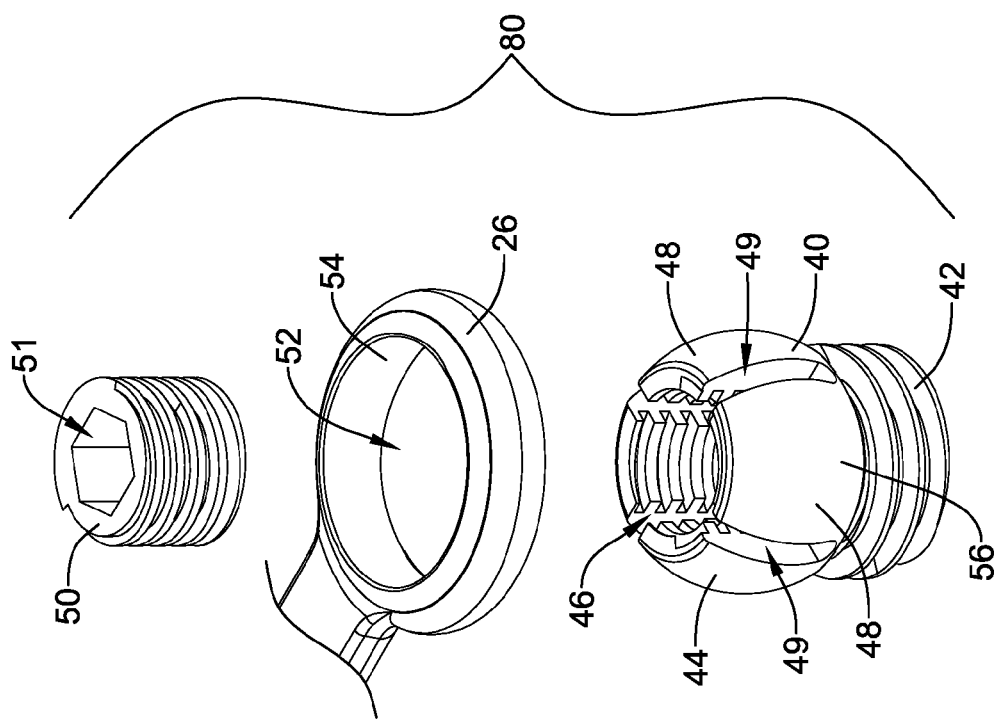
FIG. 4 is an enlarged perspective view of components of a coupling portion of the transverse connector of FIG. 2.

Turning now to FIG. 4, a coupling assembly 80 of the transverse connector 20 will be further described. It is noted that although one coupling assembly 80 at one end of the transverse connector 20 is described herein, the coupling assembly 80 at the other end of the transverse connector 20 may be similarly configured and include similar components.

The coupling assembly 80 may include the coupling housing 26, the fastener 40, and a set screw 50 configured to threadably engage a threaded bore 46 of the fastener 40. The fastener 40 may include external threading configured to threadably engage an internal threaded portion of the housing 12 of a vertebral anchor 10, and a spherical upper surface. For instance, the fastener 40 may include a lower threaded portion 42 including the external threading and an upper spherical portion 44 including a spherically convex surface 56. In some instances, the fastener 40 may be a monolithic member including the upper spherical portion 44 and the lower threaded portion 42.

The upper spherical portion 44 may include a plurality of convex segments 48 with slots 49 therebetween radially arranged. The presence of the slots 49 between adjacent segments 48 may permit the segments 48 of the upper spherical portion 44 to flex or deflect relative to each other.

Figure 6:
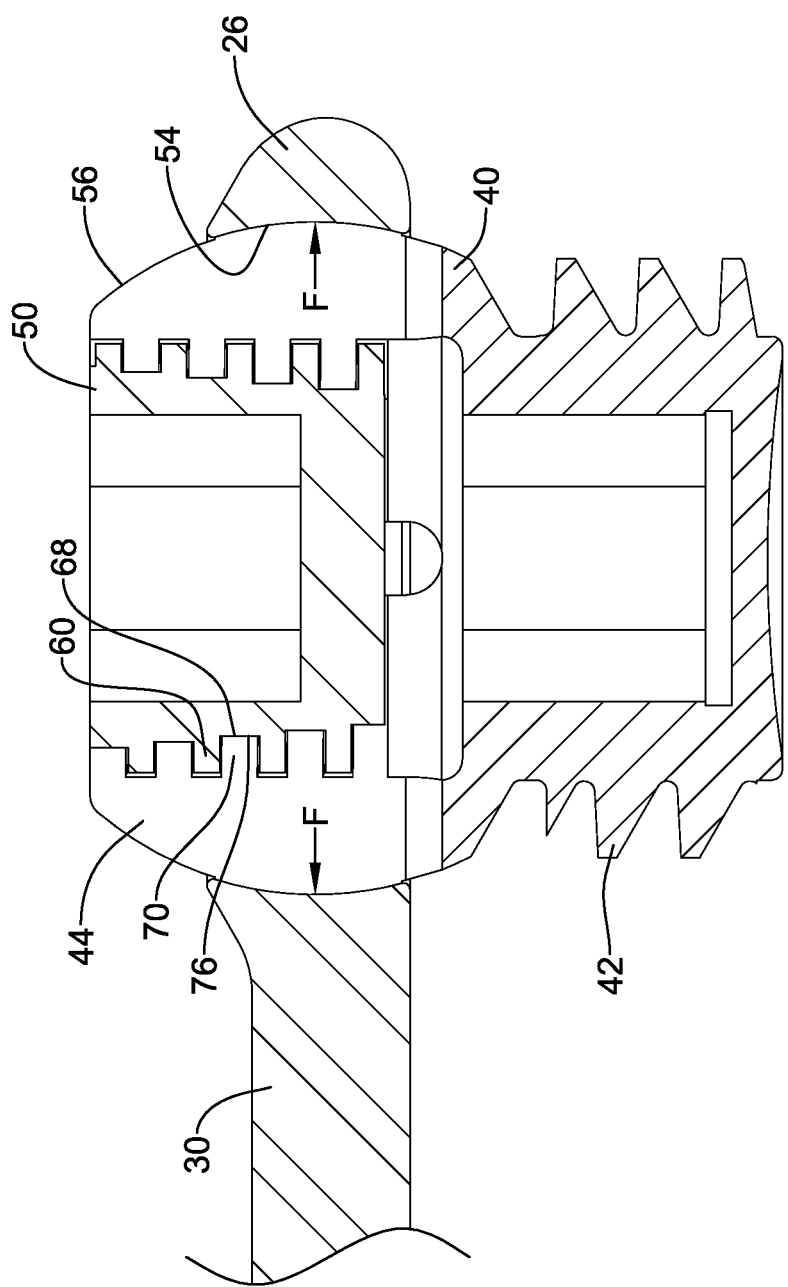
FIG. 6 is a cross-sectional view of the components of the coupling portion assembled together.

The upper spherical portion 44 may be configured to be positioned in the aperture 52 of the coupling housing 26 such that the spherically convex surface 56 faces and mates with a spherically concave annular sidewall 54 of the aperture 52. Thus, the aperture 52 may receive the upper spherical portion 44 of the fastener 40 therein to permit rotational movement therebetween. As shown in FIG. 6, the set screw 50 may be threadably disposed in the threaded bore 46 to exert a radially outward force F on the convex segments 48 of the upper spherical portion 44 to press the spherically convex surface 56 against the spherically concave surface of the annular sidewall 54 to lock the upper spherical portion 44 in the aperture 52 and prevent further rotational movement therebetween. In some instances, the set screw 50 and the fastener 40 may be configured such that the force F exerted on the convex segments 48 from the set screw 50 is substantially radially outward, without appreciable force being generated axially.

Figure 5:
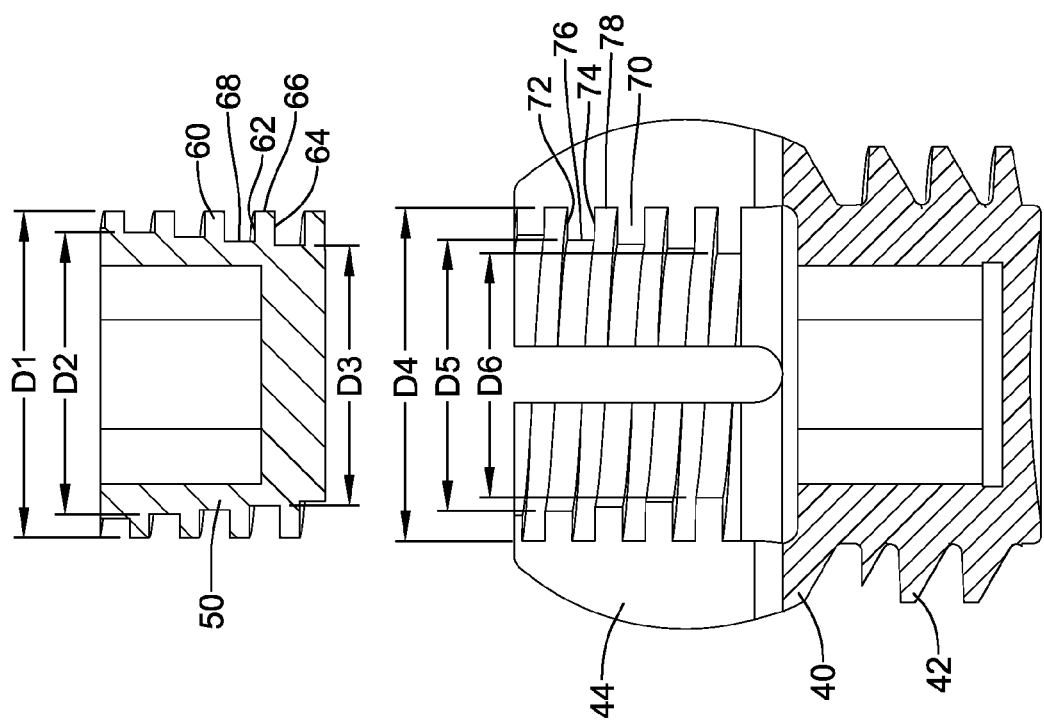
FIG. 5 is a cross-sectional view of components of the coupling portion shown in FIG. 4.

One possible configuration of the threading of the set screw 50 and the threading of the threaded bore 46 of the fastener 40 which achieves a substantially radially outward force F is illustrated at FIG. 5. In this embodiment, the set screw 50 includes an external thread 60 having a major diameter D1 that is constant from an upper portion of the set screw 50 to a lower portion of the set screw 50, and a minor diameter that tapers from a larger diameter D2 proximate the upper portion of the set screw 50 to a smaller diameter D3 proximate the lower portion of the set screw 50. Thus the height of the thread 60 increases from the upper portion to the lower portion of the set screw 50 while the major diameter D1 remains substantially constant.

Furthermore, in this embodiment, the threaded bore 46 of the upper spherical portion 44 of the fastener 40 includes an internal thread 70 that has a major diameter D4 that is constant from an upper portion of the threaded bore 46 to a lower portion of the threaded bore 46, and a minor diameter that tapers from a larger diameter D5 proximate the upper portion of the threaded bore 46 to a smaller diameter D6 proximate the lower portion of the threaded bore 46. Thus the height of the thread 70 increases from the upper portion of the threaded bore 46 to the lower portion of the threaded bore 46 while the major diameter D4 remains substantially constant.

The thread 60 of the set screw 50 may be configured such that the upper flank 62 of the thread 60 is perpendicular to the central longitudinal axis of the set screw 50 and the lower flank 64 of the thread 60 is perpendicular to the central longitudinal axis of the set screw 50. Thus, the upper flank 62 may be parallel to the lower flank 64. Furthermore, the crest 66 of the thread 60 may be perpendicular to the upper and lower flanks 62, 64 and the root 68 of the thread 60 may be perpendicular to the upper and lower flanks 62, 64. Thus, the crest 66 and/or root 68 of the thread 60 may be parallel to the central longitudinal axis of the set screw 50.

Similarly, the thread 70 of the threaded bore 46 may be configured such that the upper flank 72 of the thread 70 is perpendicular to the central longitudinal axis of the threaded bore 46 and the lower flank 74 of the thread 70 is perpendicular to the central longitudinal axis of the threaded bore 46. Thus, the upper flank 72 may be parallel to the lower flank 74. Furthermore, the crest 76 of the thread 70 may be perpendicular to the upper and lower flanks 72, 74 and the root 78 of the thread 70 may be perpendicular to the upper and lower flanks 72, 74. Thus, the crest 76 and/or root 78 of the thread 70 may be parallel to the central longitudinal axis of the threaded bore 46.

Such a configuration may provide positive engagement between the thread 60 of the set screw 50 and the thread 70 of the threaded bore 46 even at the onset of threading the set screw 50 into the threaded bore 46. In other words, the thread 60 may engage the thread 70 as the set screw 50 initially enters the threaded bore 46. As the set screw 50 is continued to be threaded into the threaded bore 46, the root 68 of the thread 60 of the set screw 50 presses against the crest 76 of the thread 70 of the threaded bore 46, exerting a radially outward force F normal to the surfaces of the root 68 and crest 76 on the convex segments 48 of the upper spherical portion 44 of the fastener 40, which in turn presses the convex segments 48 against the concave sidewall 54 of the coupling housing 26, as shown in FIG. 6. Due to the perpendicular orientation of the flanks 62/64, 72/74 and the parallel orientation of the crests 66/76 and roots 68/78 relative to the central longitudinal axes, no appreciable force is generated other than in a direction perpendicular to the central longitudinal axis.

Referring again to FIG. 3, in use, the transverse connector 20 may be coupled between first and second vertebral anchors 10. Initially, the first and second vertebral anchors 10 may be secured to a vertebra, followed by positioning an elongate member 4 in the channel 6 of the housing 12 of each of the vertebral anchors 10. With the elongate member 4 in the channel 6 of the housing 12, the fastener 40 may be threaded into the threaded opening in the housing 12 between the legs 8 of the housing 12 to secure the elongate member 4 in the channel 6. For example, the fastener 40 may include an internal driver interface 45, such as a hex socket, or other driver interface for receiving a driver to rotatably advance the fastener 40 against the elongate member 4. In some instances, the vertebral anchor 10 may include a seat 5 against which the elongate member 4 is pressed against to transfer a locking force to the head 16 of the bone screw 14 to lock the housing 12 from further pivotable movement relative to the bone screw 14. In other instances, the elongate member 4 may be pressed directly against the head 16 of the bone screw 14. This process may be followed to secure each of the elongate members 4 to the housing 12 of the respective vertebral anchor 10.

If not already coupled to the fastener 40, the first connector member 22 may then be coupled to the upper spherical portion 44 of the fastener 40 secured to the first vertebral anchor 10a and/or the second connector member 24 may be coupled to the upper spherical portion 44 of the fastener 40 secured to the second vertebral anchor 10b. The spherical interface between the spherically convex surface 56 of the upper spherical portion 44 and the spherically concave sidewall 54 of the aperture 52 of the coupling housing 26 allows for multi-axial rotation of the transverse connector 20 relative to the housings 12 to permit a desired orientation of the transverse connector 20.

With the coupling housing 26 properly oriented around the upper spherical portion 44, the set screw 50 may be threadably engaged in the threaded bore 46 of the fastener 40 to apply a radially outward locking force F between the spherically convex surface 56 of the upper spherical portion 44 and the spherically concave sidewall 54 of the aperture 52 of the coupling housing 26. This may be repeated for each end of the transverse connector 20 to fixedly lock the transverse connector 20 to the housing 12 of each vertebral anchor 10.

The locking screw 38 may also be tightened once the desired orientation between the first connector member 22 and the second connector member 24 is achieved to fix the first connector member 22 to the second connector member 24. As shown in FIG. 3, when the transverse connector 20 is secured to the housings 12 of the vertebral anchors 10, the first and second connector members 22, 24 may be spaced away from direct contact with the housings 12 of the vertebral anchors 10 such that there is a gap between the upper extent of the housings 12 and the coupling housings 26.

Figure 8:
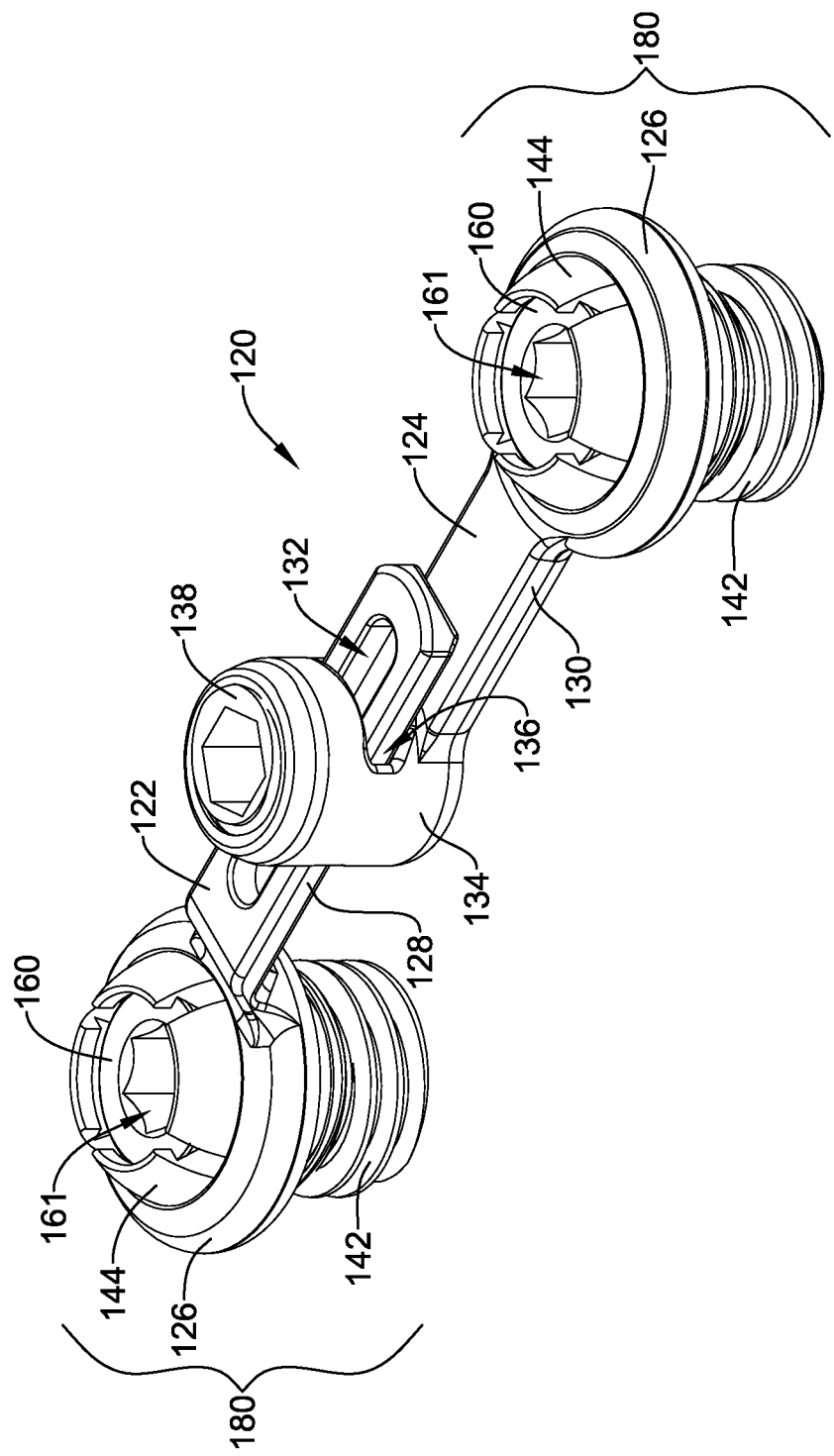
FIG. 8 is a perspective view of another transverse connector for use in a spinal stabilization system.

Another transverse connector 120, which may be coupled between the first and second vertebral anchors 10a, 10b is shown in FIG. 8. The transverse connector 120 may include a first connector member 122 and a second connector member 124 coupled together. For instance, the first connector member 122, which may be considered a male connector member, may include a coupling housing 126 and an elongate extension 128 extending from the coupling housing 126. Furthermore, the second connector member 124, which may be considered a female connector member, may include a coupling housing 126 and an elongate extension 130 extending from the coupling housing 126. The elongate extension 130 may include a receiver 134 with an opening 136 therethrough for receiving the elongate extension 128 of the first connector member 122.

The transverse connector 120 may be configured such that the first connector member 122 may be adjustable relative to the second connector member 124. For example, the first connector member 122 may translate along a longitudinal axis relative to the second connector member 124, in some instances. When the first connector member 122 is positioned at a desired orientation relative to the second connector member 124, the locking screw 138, threadably engaged in a threaded bore of the receiver 134, may be rotated into engagement against the elongate extension 128 of the first connector member 122 to apply a clamping force between the first connector member 122 and the second connector member 124 to thereby prevent further movement therebetween.

Figure 9:
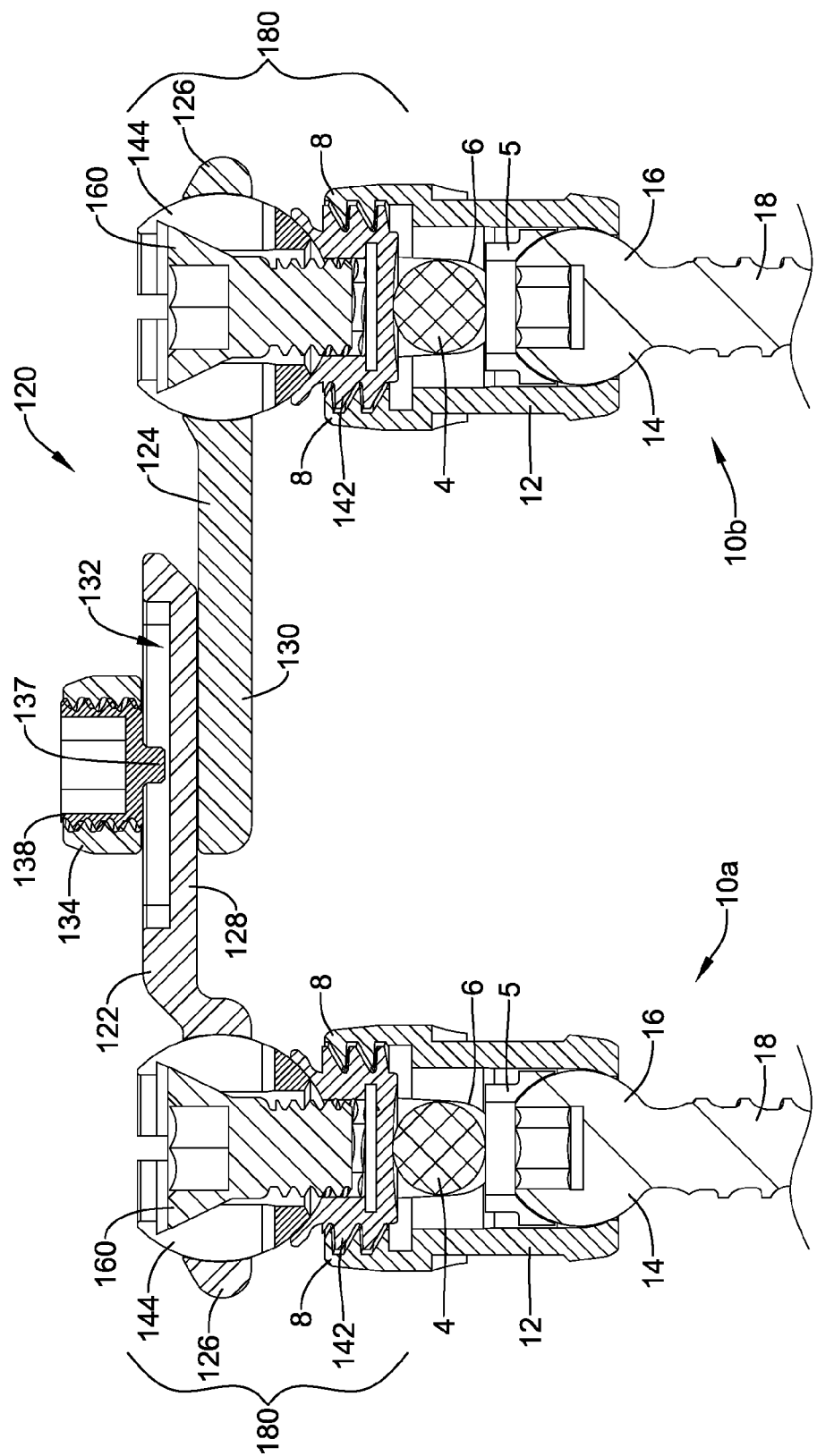
FIG. 9 is a cross-sectional view of the transverse connector of FIG. 8.

Referring to FIG. 9, the locking screw 138 may include a protuberance 137 extending into an elongate recess 132 of the elongate extension 128 of the first connector member 122. The recess 132 may include end surfaces which limit the longitudinal travel of the protuberance 137 in the recess 132, and thus prevent decoupling of the first connector member 122 from the second connector member 124.

The transverse connector 120 may include coupling assemblies 180 configured to secure the transverse connector 120 to the housings 12 of vertebral anchors 10. As shown in FIG. 9, a first coupling assembly 180 proximate the first end of the transverse connector 120 may couple the transverse connector 120 to a first vertebral anchor 10a and a second coupling assembly 180 proximate the second end of the transverse connector 120 may couple the transverse connector 120 to a second vertebral anchor 10b.

Figure 10:
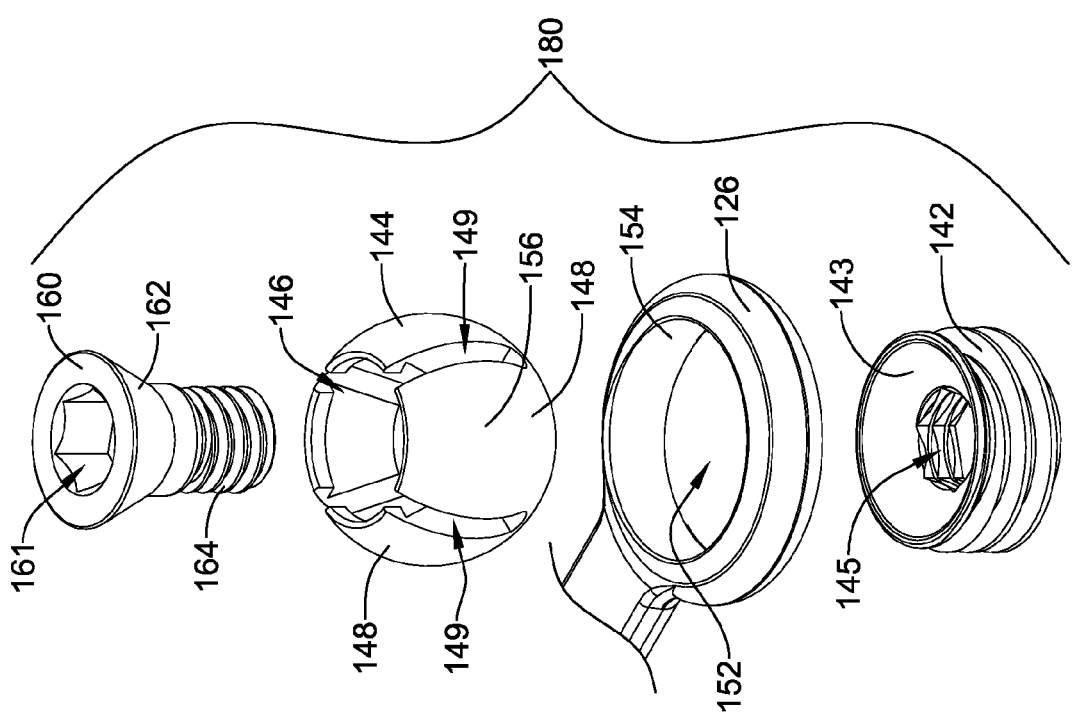
FIG. 10 is an enlarged perspective view of components of a coupling portion of the transverse connector of FIG. 8.

Turning now to FIG. 10, a coupling assembly 180 of the transverse connector 120 will be further described. It is noted that although one coupling assembly 180 at one end of the transverse connector 120 is described herein, the coupling assembly 180 at the other end of the transverse connector 120 may be similarly configured and include similar components.

The coupling assembly 180 may include the coupling housing 126, a threaded fastener 142, a spherical member 144, and a tapered screw 160 configured to threadably engage a threaded bore 145 of the fastener 142. The fastener 142 may include external threading configured to threadably engage an internal threaded portion of the housing 12 of a vertebral anchor 10 to secure an elongate member 4 in the channel 6 of the housing 12. The upper surface of the fastener 142 may be a spherically concave upper surface 143.

The spherical member 144 may include a plurality of convex segments 148 with slots 149 therebetween radially arranged. The presence of the slots 149 between adjacent segments 148 may permit the segments 148 of the spherical member 144 to flex or deflect relative to each other.

The spherical member 144 may be configured to be positioned in the aperture 152 of the coupling housing 126 such that the spherically convex surface 156 faces and mates with a spherically concave annular sidewall 154 of the aperture 152. Thus, the aperture 152 may receive the spherical member 144 therein to permit rotational movement therebetween. The spherically convex surface 156 is also configured to rest against and mate with the spherically concave surface 143 of the fastener 142.

Figure 11:
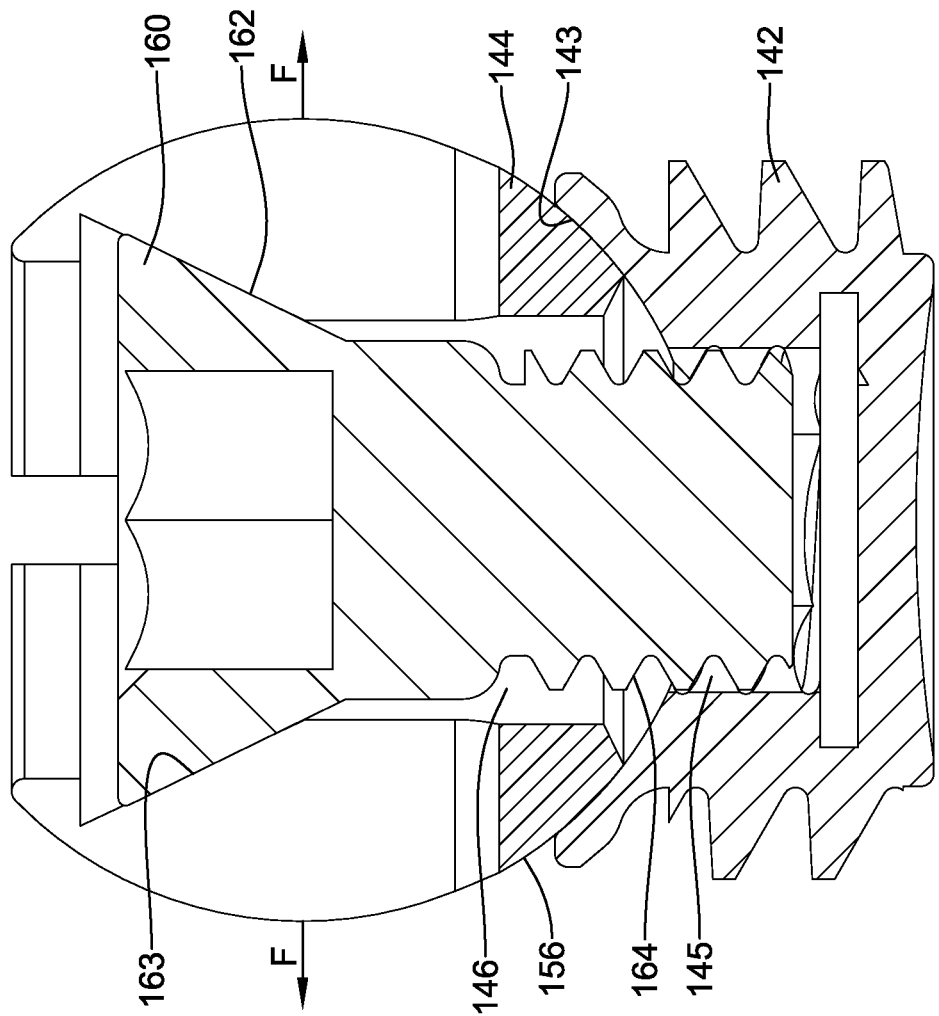
FIG. 11 is a cross-sectional view of components of the coupling portion shown in FIG. 10.

As shown in FIG. 11, a tapered screw 160 may be inserted through the bore 146 of the spherical member 144 such that a threaded portion 164 of the tapered screw threadably engages the threaded bore 145 of the fastener 142. A tapered head portion 162 of the tapered screw 160 may contact a tapered surface 163 of the bore 146 of the spherical member 144 to exert a radially outward force on the convex segments 148 of the spherical member 144 when the tapered screw 160 is threadedably engaged with the fastener 142. The tapered screw 160 may include an internal driver interface 161, such as a hex socket, or other driver interface for receiving a driver to rotatably advance the tapered screw 160 into the threaded bore 145 such that the tapered head portion 162 presses against the tapered surface 153 of the bore 146.

Referring again to FIG. 9, in use, the transverse connector 120 may be coupled between first and second vertebral anchors 10. Initially, the first and second vertebral anchors 10 may be secured to a vertebra, followed by positioning an elongate member 4 in the channel 6 of the housing 12 of each of the vertebral anchors 10. With the elongate member 4 in the channel 6 of the housing 12, the fastener 142 may be threaded into the threaded opening in the housing 12 between the legs 8 of the housing 12 to secure the elongate member 4 in the channel 6. For example, the fastener 142 may include an internal driver interface, such as a hex socket, or other driver interface formed in the threaded bore 145 for receiving a driver to rotatably advance the fastener 142 against the elongate member 4.

Figure 12:
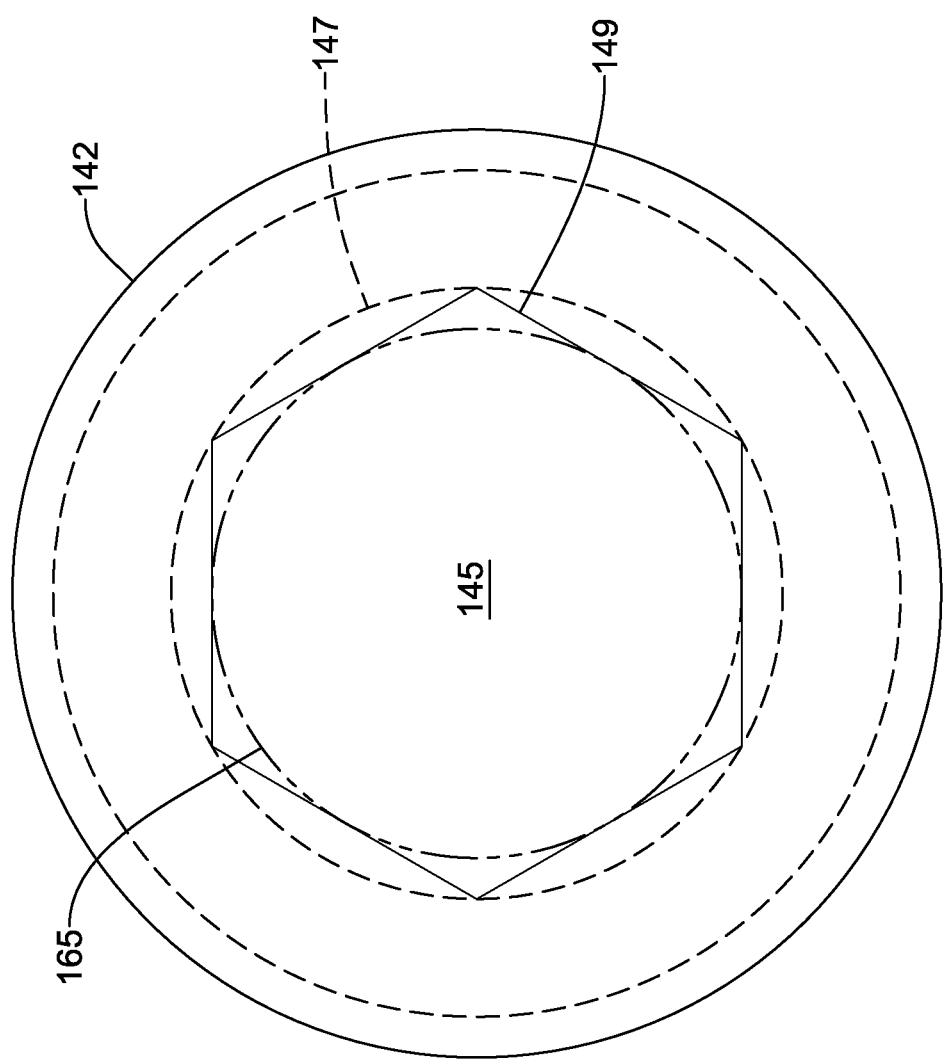
FIG. 12 is a top view of the set screw of the transverse connector of FIG. 8.

As shown in FIG. 12, the bore 145 may be configured with hexagonal sidewalls 149 defining the internal driver interface for receiving a hex wrench. The threading of the bore 145 may be configured such that the major diameter 147 of the internal threading of the bore 145 circumscribes the hexagonal sidewalls 149, while the minor diameter 165 of the threaded portion 164 of the tapered screw 160 would be inscribed within the hexagonal sidewalls 149. It is contemplated that the driver interface may be otherwise configured into the bore 145 while preserving the internal threading for threadably receiving the threaded portion 164 of the tapered screw 160.

The spherical member 144, rotatably coupled in the coupling housing 126 of the first connector member 122 and/or the second connector member 124, may then be positioned against the spherically concave upper surface 143 of the fastener 142 secured to the respective vertebral anchor 10. The spherical interface between the spherically convex surface 156 of the spherical member 144 and the spherically concave sidewall 154 of the aperture 152 of the coupling housing 126 allows for multi-axial rotation of the transverse connector 120 relative to the housings 12 to permit a desired orientation of the transverse connector 120.

With the spherically convex surface 156 of the spherical member 144 positioned against the spherically concave upper surface 143 of the fastener 142, the tapered screw 160 may be advanced through the bore 146 of the spherical member 144 and threadably engaged in the threaded bore 145 of the fastener 142 to apply a radially outward locking force F between the spherically convex surface 156 of the spherical member 144 and the spherically concave sidewall 154 of the aperture 152 of the coupling housing 126. This may be repeated for each end of the transverse connector 120 to fixedly lock the transverse connector 120 to the housing 12 of each vertebral anchor 10.

The locking screw 138 may also be tightened once the desired orientation between the first connector member 122 and the second connector member 124 is achieved to fix the first connector member 122 to the second connector member 124. As shown in FIG. 9, when the transverse connector 120 is secured to the housings 12 of the vertebral anchors 10, the first and second connector members 122, 124 may be spaced away from direct contact with the housings 12 of the vertebral anchors 10 such that there is a gap between the upper extent of the housings 12 and the coupling housings 126.

Figure 13:
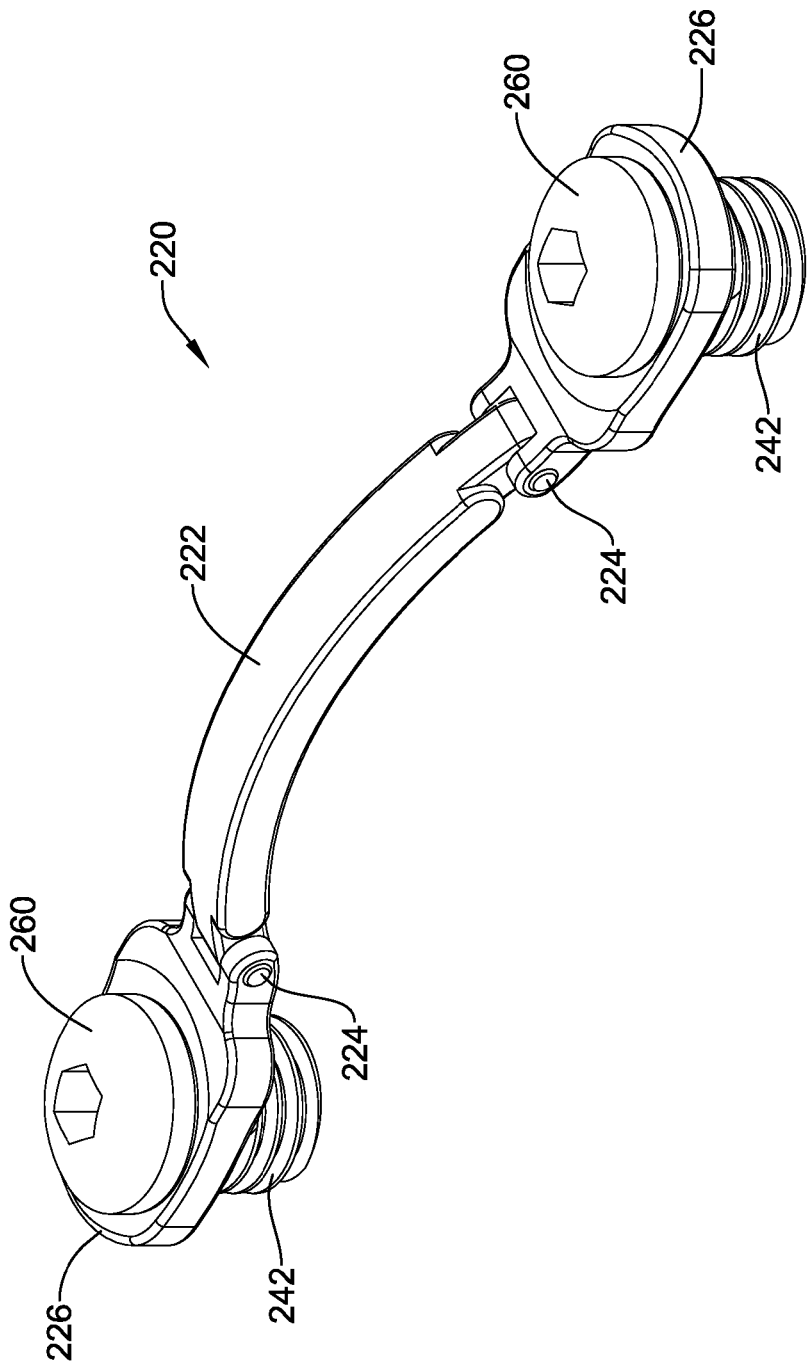
FIG. 13 is a perspective view of another transverse connector for use in a spinal stabilization system.

Another transverse connector 220, which may be coupled between the first and second vertebral anchors 10a, 10b is shown in FIG. 13. The transverse connector 220 may include a first coupling housing 226, a second coupling housing 226 and a cross member 222 pivotably coupled to each of the coupling housings 226 at a pivot point, such as at pins 224.

Figure 14:
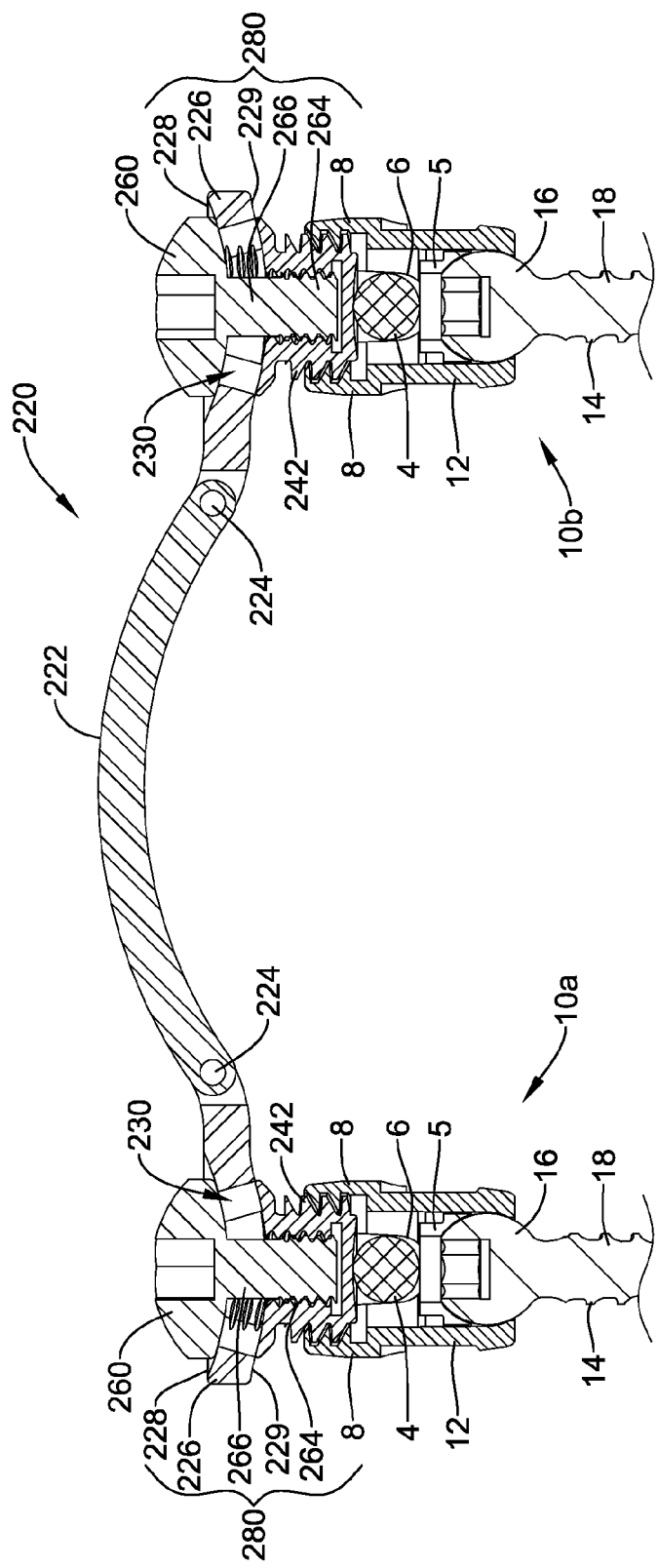
FIG. 14 is a cross-sectional view of the transverse connector of FIG. 13.

The transverse connector 220 may include coupling assemblies 280 configured to secure the transverse connector 220 to the housings 12 of vertebral anchors 10. As shown in FIG. 14, a first coupling assembly 280 proximate the first end of the transverse connector 220 may couple the transverse connector 220 to a first vertebral anchor 10a and a second coupling assembly 280 proximate the second end of the transverse connector 220 may couple the transverse connector 220 to a second vertebral anchor 10b.

Figure 15:
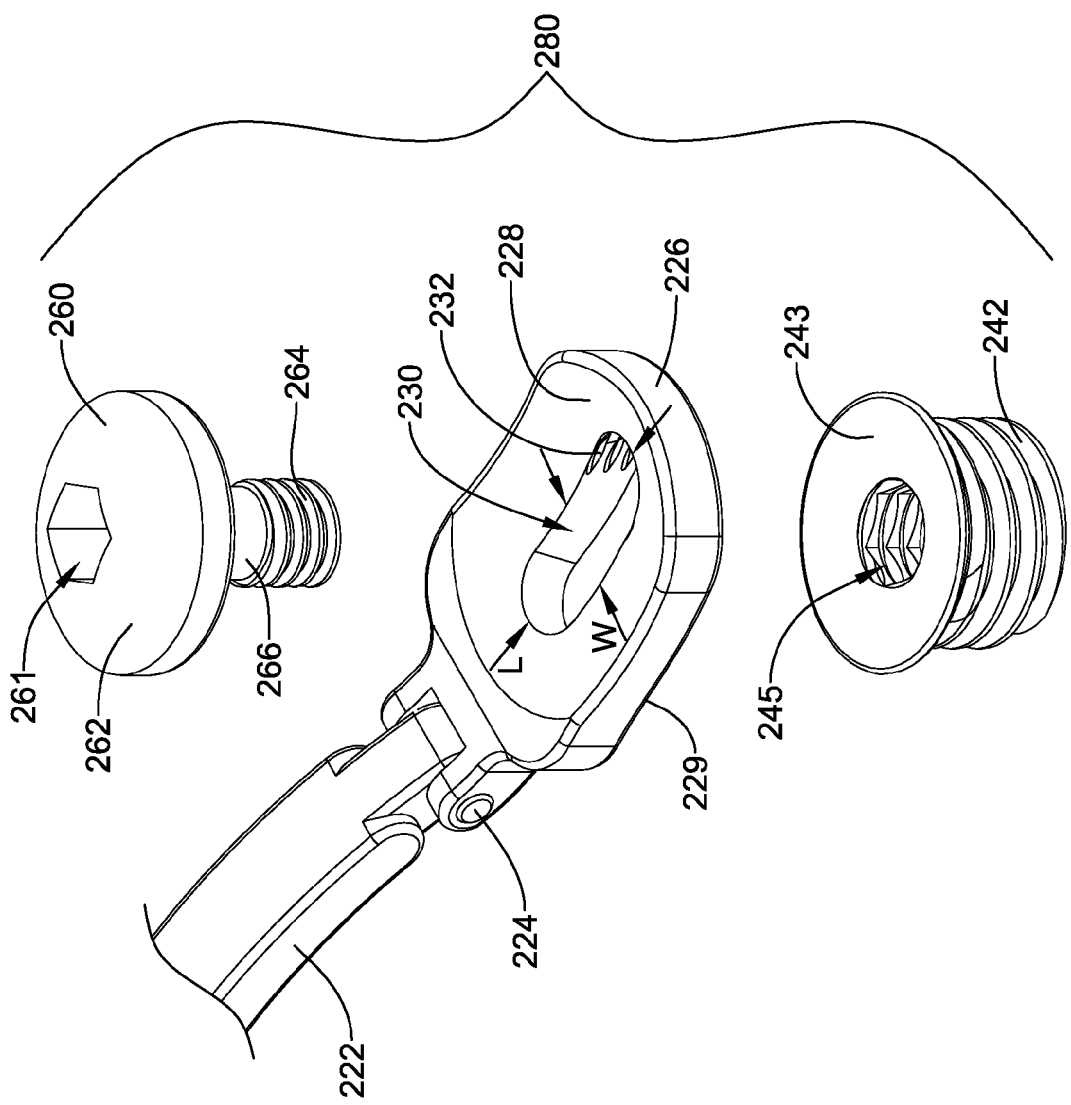
FIG. 15 is an enlarged perspective view of components of a coupling portion of the transverse connector of FIG. 13.

Turning now to FIG. 15, a coupling assembly 280 of the transverse connector 220 will be further described. It is noted that although one coupling assembly 280 at one end of the transverse connector 220 is described herein, the coupling assembly 280 at the other end of the transverse connector 220 may be similarly configured and include similar components.

The coupling assembly 280 may include the coupling housing 226, a threaded fastener 242, and a threaded screw 260 configured to extend through the elongated opening 230 and threadably engage a threaded bore 245 of the fastener 242. The fastener 242 may include external threading configured to threadably engage an internal threaded portion of the housing 12 of a vertebral anchor 10 to secure an elongate member 4 in the channel 6 of the housing 12. The upper surface of the fastener 242 may be a spherically concave upper surface 243.

The coupling housing 226 may include an upper surface 228 such as a spherically concave surface, a lower surface 229 such as a spherically convex surface, and an aperture extending through the coupling housing 226 from the upper surface 228 to the lower surface 229. In some instances, the aperture may be an elongated opening 230 having a width W and a length L greater than the width W. The elongated opening 230 may include partial threading 232 along a portion of the sidewall of the elongated opening 230. For example, each of two opposing sidewalls of the elongated opening 230 may include discontinuous threads.

The threaded screw 260 may include a head 262 having a driver interface 261 and a shank extending from the head 262 having a threaded lower portion 264 and an unthreaded upper portion 266. The threaded lower portion 264 may be sized to pass through the elongate opening 230 of the coupling housing 226 only by way of the partial threads 228 of the elongate opening 230. In other words, the major diameter of the threaded lower portion 264 may be greater than the width W of the elongate opening 230 such that the threaded lower portion 264 cannot pass freely through the elongate opening 230 in an axial direction without being rotatably threaded through the partial threaded portion of the elongated opening 230. The unthreaded upper portion 266 may have a diameter less than the width W of the elongated opening 230 such that once the lower threaded portion 264 is threaded through the elongated opening 230, the unthreaded upper portion 266 (which is now positioned in the elongated opening 230) may freely travel back and forth along the length L of the elongated opening 230 to any desired position.

Referring again to FIG. 14, in use, the transverse connector 220 may be coupled between first and second vertebral anchors 10. Initially, the first and second vertebral anchors 10 may be secured to a vertebra, followed by positioning an elongate member 4 in the channel 6 of the housing 12 of each of the vertebral anchors 10. With the elongate member 4 in the channel 6 of the housing 12, the fastener 242 may be threaded into the threaded opening in the housing 12 between the legs 8 of the housing 12 to secure the elongate member 4 in the channel 6. For example, similar to the fastener 142 discussed above, the fastener 242 may include an internal driver interface, such as a hex socket, or other driver interface formed in the threaded bore 245 for receiving a driver to rotatably advance the fastener 242 against the elongate member 4.

The spherically convex lower surface 229 of the coupling housing 226 may then be positioned against the spherically concave upper surface 243 of the fastener 242 secured to the respective vertebral anchor 10, and the threaded screw 260 (extending through the elongated opening 230) may be threaded into the threaded bore 245 of the fastener 242. The spherical interface between the spherically convex lower surface 229 of the coupling housing 226 and the spherically concave upper surface 243 of the fastener 242 allows for multi-axial rotation of the transverse connector 220 relative to the housings 12 while the unthreaded upper portion 266 of the threaded screw 260 travels along the elongated opening 230 to permit a desired orientation of the transverse connector 220. In some instances, the under side of the head 262 of the threaded screw 260 may be spherically convex to mate with the spherically concave upper surface 228 of the coupling housing 226. The spherical interfaces and elongated opening 230, along with the pivotable connection between the coupling housing 226 and the cross member 222, may allow for a desired degree of lateral adjustability of the transverse connector 220.

Once in a desired orientation with the spherically convex lower surface 229 of the coupling housing 226 positioned against the spherically concave upper surface 243 of the fastener 242, the threaded screw 260 may be rotated in the threaded bore 245 of the fastener 242 to apply a locking force between the spherically convex lower surface 229 of the coupling housing 226 and the spherically concave upper surface 243 of the fastener 242 to lock the coupling housing 226 from further movement relative to the housing 12. This may be repeated for each end of the transverse connector 220 to fixedly lock the transverse connector 220 to the housing 12 of each vertebral anchor 10.

As shown in FIG. 14, when the transverse connector 220 is secured to the housings 12 of the vertebral anchors 10, the coupling housings 226 of the transverse connector 220 may be spaced away from direct contact with the housings 12 of the vertebral anchors 10 such that there is a gap between the upper extent of the housings 12 and the coupling housings 226.

Figure 16:
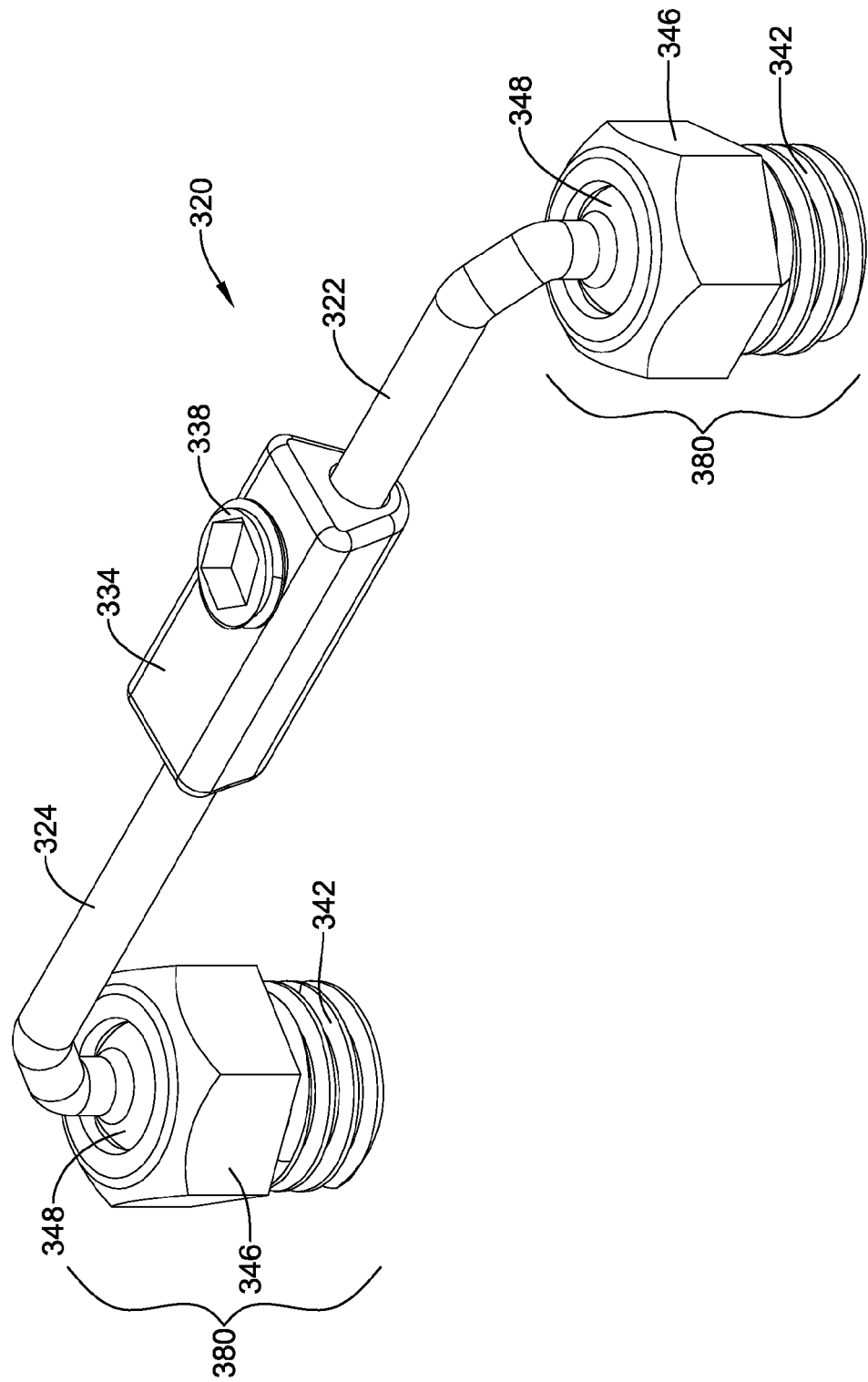
FIG. 16 is a perspective view of yet another transverse connector for use in a spinal stabilization system.

Yet another transverse connector 320, which may be coupled between the first and second vertebral anchors 10 is shown in FIG. 16. The transverse connector 320 may include a first connector member 322 and a second connector member 324 coupled together. For instance, the first connector member 322, which may be considered a male connector member, may include a first spherical member 348 and an elongate extension 328 extending from the first spherical member 348. Furthermore, the second connector member 324, which may be considered a female connector member, may include a second spherical member 348 and an elongate extension 330 extending from the second spherical member 348. The elongate extension 330 may include a receiver 334 with an opening extending therein for receiving the elongate extension 328 of the first connector member 322.

The transverse connector 320 may be configured such that the first connector member 322 may be adjustable relative to the second connector member 324. For example, the first connector member 322 may translate along a longitudinal axis relative to the second connector member 324, in some instances. When the first connector member 322 is positioned at a desired orientation relative to the second connector member 326, the locking screw 338, threadably engaged in a threaded bore of the receiver 334, may be rotated into engagement against the elongate extension 328 of the first connector member 322 to apply a clamping force between the first connector member 322 and the second connector member 324 to thereby prevent further movement therebetween.

Figure 17:
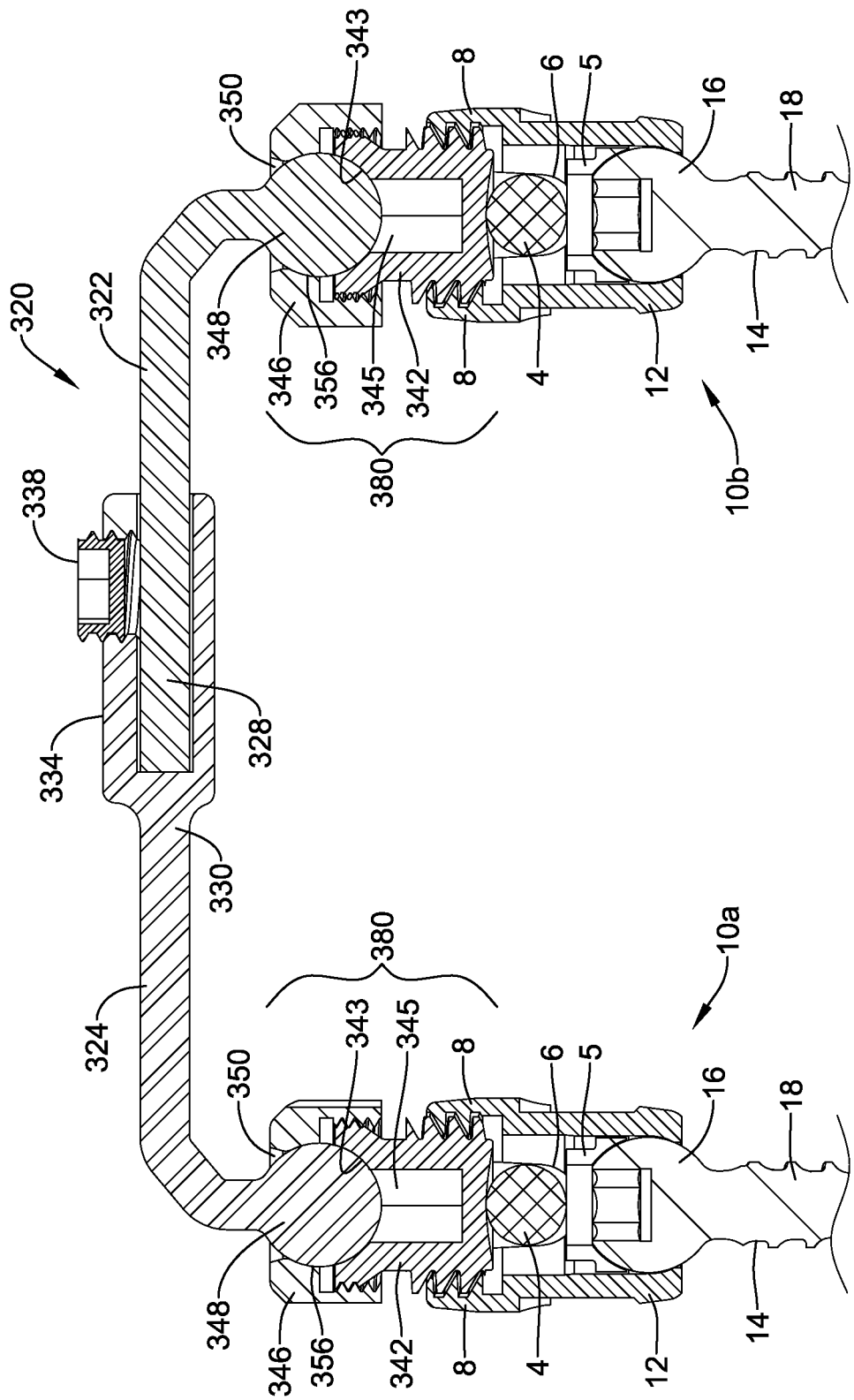
FIG. 17 is a cross-sectional view of the transverse connector of FIG. 16.

The transverse connector 320 may include coupling assemblies 380 configured to secure the transverse connector 320 to the housings 12 of vertebral anchors 10. As shown in FIG. 17, a first coupling assembly 380 proximate the first end of the transverse connector 320 may couple the transverse connector 320 to a first vertebral anchor 10a and a second coupling assembly 380 proximate the second end of the transverse connector 320 may couple the transverse connector 320 to a second vertebral anchor 10b.

A coupling assembly 380 may include the spherical member 348, a threaded fastener 342, and a threaded nut 346 configured to threadably engage a threaded upper portion of the fastener 342. The fastener 342 may also include a lower portion having external threading configured to threadably engage an internal threaded portion of the housing 12 of a vertebral anchor 10 to secure an elongate member 4 in the channel 6 of the housing 12. The upper surface of the fastener 342 may be a spherically concave upper surface 343.

The threaded nut 346 may surround at least a portion of the spherical member 348 with the extension 328/330 extending through a bore 350 of the threaded nut 346. The spherical member 348 may be sized larger than the bore 350 of the threaded nut 346 such that the spherical member 348 cannot pass through the bore 350. A sidewall of the bore 350 of the nut 346 may be configured to engage a portion of the spherical member 348 when the threaded nut 346 is tightened onto the fastener 342.

The spherical member 348 may include a spherically convex surface 356 configured to rest against and mate with the spherically concave surface 343 of the fastener 342 to provide multi-axial rotational orientation therebetween.

In use, the transverse connector 320 may be coupled between first and second vertebral anchors 10. Initially, the first and second vertebral anchors 10 may be secured to a vertebra, followed by positioning an elongate member 4 in the channel 6 of the housing 12 of each of the vertebral anchors 10. With the elongate member 4 in the channel 6 of the housing 12, the fastener 342 may be threaded into the threaded opening in the housing 12 between the legs 8 of the housing 12 to secure the elongate member 4 in the channel 6. For example, the fastener 342 may include an internal driver interface 345, such as a hex socket, or other driver interface for receiving a driver to rotatably advance the fastener 342 against the elongate member 4.

The spherical member 348 may then be positioned against the spherically concave upper surface 343 of the fastener 342 secured to the respective vertebral anchor 10. The spherical interface between the spherically convex surface 356 of the spherical member 348 and the spherically concave upper surface 343 allows for multi-axial rotation of the transverse connector 320 relative to the housings 12 to permit a desired orientation of the transverse connector 320.

With the spherically convex surface 356 of the spherical member 348 positioned against the spherically concave upper surface 343 of the fastener 342, the threaded nut 346 may be threadably engaged onto the threaded upper portion of the fastener 342 to apply a locking force between the spherically convex surface 356 of the spherical member 348 and the spherically concave upper surface 343 of the fastener 342. This may be repeated for each end of the transverse connector 320 to fixedly lock the transverse connector 320 to the housing 12 of each vertebral anchor 10.

The locking screw 338 may also be tightened once the desired orientation between the first connector member 322 and the second connector member 324 is achieved to fix the first connector member 322 to the second connector member 324. As shown in FIG. 17, when the transverse connector 320 is secured to the housings 12 of the vertebral anchors 10, the first and second connector members 322, 324 may be spaced away from direct contact with the housings 12 of the vertebral anchors 10 such that there is a gap between the upper extent of the housings 12 and the threaded nuts 346.

Figure 18:
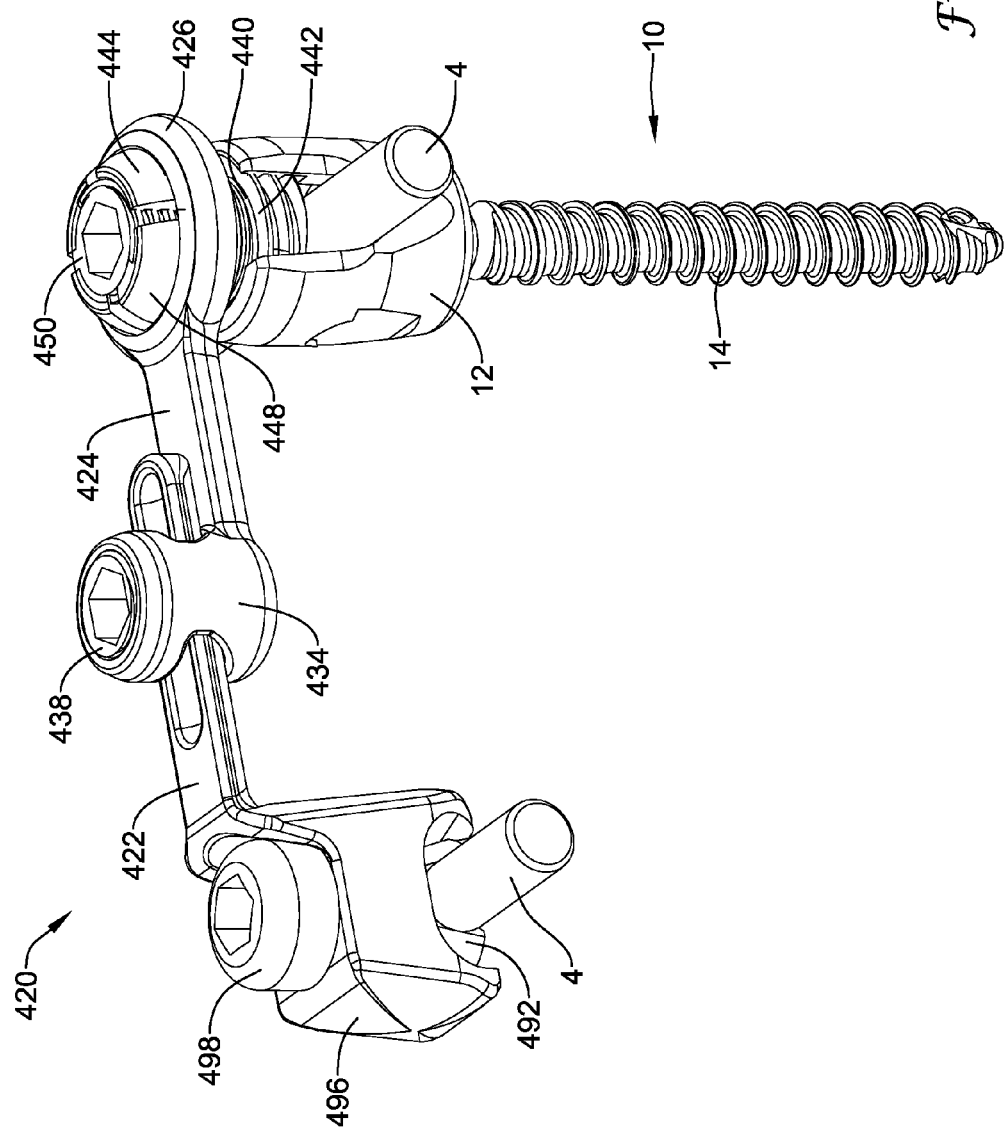
FIG. 18 is a perspective view of another transverse connector for use in a spinal stabilization system.

In some instances, it may be desirable to provide a transverse connector having a first end including a coupling assembly for coupling to a housing 12 of a vertebral anchor 10 and a second end including a coupling assembly for coupling directly to an elongate member 4. One such example of a transverse connector 420, which may be coupled between a vertebral anchor 10 and an elongate member 4 is shown in FIG. 18. The transverse connector 420 may include a first connector member 422 and a second connector member 424 coupled together. Similar to transverse connectors discussed above, the transverse connector 420 may be configured such that the first connector member 422 may be adjustable relative to the second connector member 424. When the first connector member 422 is positioned at a desired orientation relative to the second connector member 424, the locking screw 438, threadably engaged in a threaded bore of the receiver 434, may be rotated into engagement against the elongate extension 428 of the first connector member 422 to apply a clamping force between the first connector member 422 and the second connector member 424 to thereby prevent further movement therebetween. It is noted that, alternatively, the receiver 434 may be associated with the first connector member 422 and the elongate extension 428 may be associated with the second connector member 424, or the first and second connector members 422, 424 may otherwise be configured to be adjustably secured to another.

The transverse connector 420 may include a coupling assembly at one end of the transverse connector 420 configured to secure the first end of the transverse connector 420 to the housing 12 of a vertebral anchor 10 and a dissimilar coupling assembly at the other end of the transverse connector 420 configured to secure the second end of the transverse connector 420 to the elongate member 4.

The first coupling assembly 480 at the first end of the transverse connector 420 may be similar to one of the coupling assemblies described above in regards to the transverse connectors 20, 120, 220, 320. For example, as illustrated the first coupling assembly 480 may be similar to the coupling assembly 80 of the transverse connector 20, although the coupling assembly 480 may alternatively be constructed similar to the coupling assemblies 180, 280, 380, or other desired construction. Although the first coupling assembly 480 is shown associated with the second connector member 424, in other embodiments the first coupling assembly 480 may be associated with the first connector member 422.

Figure 19:
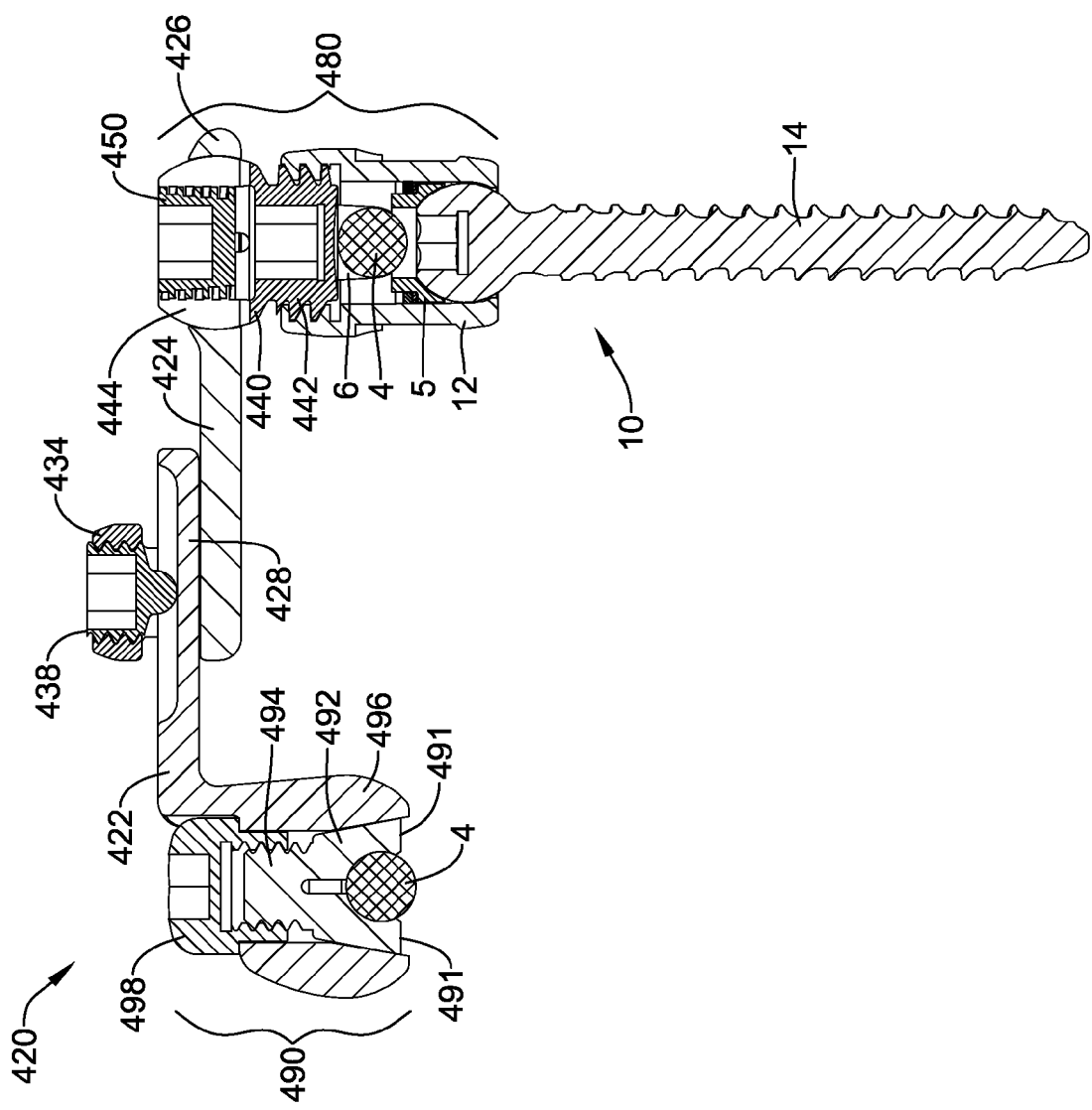
FIG. 19 is a cross-sectional view of the transverse connector of FIG. 18.

As shown in FIG. 19, the first coupling assembly 480 may include a coupling housing 426, a fastener 440, and a set screw 450 configured to threadably engage a threaded bore of the fastener 440. The fastener 440 may include external threading configured to threadably engage an internal threaded portion of the housing 12 of the vertebral anchor 10, and a spherical upper surface. For instance, the fastener 440 may include a lower threaded portion 442 including the external threading and an upper spherical portion 444 including a plurality of convex segments 448 with slots therebetween radially arranged which are flexible or deflectable relative to each other.

The upper spherical portion 444 may be configured to be positioned in the aperture of the coupling housing 426 such that the spherically convex surface of the upper spherical portion 444 faces and mates with a spherically concave annular sidewall of the aperture to permit rotational movement therebetween. The set screw 450 may be threadably disposed in the threaded bore to press the convex segments 448 against the coupling housing 426 to lock the upper spherical portion 444 in the aperture and prevent further rotational movement therebetween.

The second coupling assembly 490 at the second end of the transverse connector 420 may be configured to be secured directly to an elongate member 4. For instance, as shown in FIG. 19, the second coupling assembly 490 may include a coupler 492 having a pair of deflectable arms 491 and a threaded portion 494. The coupler 492 may be disposed in a bore of a coupling housing 496. A threaded fastener 498 may be threadably engaged with the threaded portion 494 of the coupler 492. The deflectable arms 491 may be configured to be deflected around the elongate member 4 to couple the elongate member 4 thereto. Although the second coupling assembly 490 is shown associated with the first connector member 422, in other embodiments the second coupling assembly 490 may be associated with the second connector member 424.

In use, the first coupling assembly 480 of the transverse connector 420 may be coupled to the vertebral anchor 10 as described above. Turning to the second coupling assembly 490, the second coupling assembly 490 of the transverse connector 420 may be coupled to the elongate member 4 by first inserting the elongate member 4 into the cavity between the deflectable arms 491. In some instances the elongate member 4 may snap into the cavity between the deflectable arms 491 to provisionally lock the elongate member 4 to the second coupling assembly 490. The threaded fastener 498, threadably engaged with the threaded portion 494 of the coupler 492, may then be rotated to draw the coupler 492 upward into the cavity of the coupling housing 496. As the coupler 492 is drawn upward in the coupling housing 496, the deflectable arms 491 may press against the coupling housing 496 in the bore to clamp onto the elongate member 4, thereby securing the coupling housing 490 to the elongate member 4.

Referring to any of the preceding embodiments, in some instances a locking feature may be included to prevent the threaded fastener (e.g., fastener 40, 142, 242, 342, 440) from backing out of the housing 12 of the vertebral anchor 10 when subjected to torque exerted by the transverse connector through spinal movement. For instance, an engaging member (e.g., setscrew 50, 450, threaded screw 160, 260 or spherical member 348) may be pressed against a feature of the fastener to deform the threads to lock the fastener in place. One of skill in the art will recognize that other locking features may be used to lock the threaded fastener from backing out of the housing 12 once assembled. For instance, the coupling housings may include features designed to insert into or otherwise interact with the channels 6 of the housing 12 or other feature of the housing 12 to prevent relative rotational movement therebetween.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A transverse connector for coupling between first and second vertebral anchors of a spinal stabilization system, the transverse connector comprising:
   a first coupling assembly proximate a first end of the transverse connector;
   a second coupling assembly proximate a second end of the transverse connector;
   a first fastener having external threading configured to threadably engage an internal threaded portion of a housing of the first vertebral anchor, the first fastener including a spherical upper surface;
   a second fastener having external threading configured to threadably engage an internal threaded portion of a housing of the second vertebral anchor, the second fastener including a spherical upper surface;
   wherein a spherical surface of the first coupling assembly mates with the spherical upper surface of the first fastener and a spherical surface of the second coupling assembly mates with the spherical upper surface of the second fastener;
   wherein each of the first and second fasteners is a monolithic member including an upper spherical portion including the spherical upper surface and a lower threaded portion including the external threading;
   wherein the upper spherical portion includes a threaded bore extending along a longitudinal axis of each of the first and second fasteners, the threaded bore having a major diameter that is constant from an upper portion of the threaded bore to a lower portion of the threaded bore, and a minor diameter that tapers from a larger diameter proximate the upper portion of the threaded bore to a smaller diameter proximate the lower portion of the threaded bore; and
   wherein the threaded bore includes a thread having a crest defining the minor diameter, where the crest includes a planar surface parallel to the longitudinal axis.

2. The transverse connector of claim 1, wherein each of the first and second coupling assemblies includes a coupling housing having an aperture therethrough receiving the upper spherical portion of the first or second fastener, respectively, therein.

3. The transverse connector of claim 2, further comprising:
a set screw threadably received in the threaded bore of the upper spherical portion of each of the first and second fasteners configured to exert a radially outward force on the upper spherical portion to prevent rotation of the upper spherical portion in the aperture of the respective coupling housing.

4. The transverse connector of claim 3, wherein the set screw includes external threading having a major diameter that is constant from an upper portion of the set screw to a lower portion of the set screw, and a minor diameter that tapers from a larger diameter proximate the upper portion of the set screw to a smaller diameter proximate the lower portion of the set screw.

5. The transverse connector of claim 3, wherein the threaded bore of each of the first and second fasteners includes a root defining a major diameter;
wherein the set screw includes a thread having a root defining a minor diameter and a crest defining a major diameter;
wherein a portion of the root of the set screw contacts a portion of the crest of one of the threaded bores of the first and second fasteners; and
wherein a portion of the crest of the set screw within the one of the threaded bores is spaced from the root of the one of the threaded bores of the first and second fasteners when the root of the set screw contacts a portion of the crest of the one of the threaded bores of the first and second fasteners.

6. The transverse connector of claim 4, wherein the set screw is configured to exert the radially outward force on the upper spherical portion without generating appreciable force axially.

7. The transverse connector of claim 1, wherein the first fastener is configured to secure a first elongate member in the housing of the first vertebral anchor and the second fastener is configured to secure a second elongate member in the housing of the second vertebral anchor.

8. The transverse connector of claim 1, wherein the threaded bore of each of the first and second fasteners includes a root defining the major diameter and parallel upper and lower flanks extending from the crest to the root.

9. The transverse connector of claim 8, wherein the upper and lower flanks are oriented substantially perpendicular to the longitudinal axis.

10. The transverse connector of claim 1, wherein the threaded bore of each of the first and second fasteners includes a root defining a major diameter, where the root is substantially parallel to the crest.

11. A spinal stabilization system comprising:
a first elongate member;
a second elongate member;
a first vertebral anchor including a housing and a bone engagement portion extending from the housing;
a second vertebral anchor including a housing and a bone engagement portion extending from the housing;
a third vertebral anchor including a housing and a bone engagement portion extending from the housing;
a fourth vertebral anchor including a housing and a bone engagement portion extending from the housing;
the first elongate member extending between the first and third vertebral anchors;
the second elongate member extending between the second and fourth vertebral anchors;
a first fastener securing the first elongate member in a channel of the housing of the first vertebral anchor, the first fastener including a spherical upper portion having a threaded bore disposed therein and a spherically convex surface, and a threaded lower portion threadably engaging the housing of the first vertebral anchor;
a second fastener securing the second elongate member in a channel of the housing of the second vertebral anchor, the second fastener including a spherical upper portion having a threaded bore disposed therein and a spherically convex surface, and a threaded lower portion threadably engaging the housing of the second vertebral anchor;
a transverse connector including a first coupling housing proximate a first end of the transverse connector and a second coupling housing proximate a second end of the transverse connector;
the first coupling housing including an aperture therethrough for receiving the spherical upper portion of the first fastener, the aperture having a concave annular sidewall configured to mate with the spherically convex surface of the spherical upper portion of the first fastener to allow rotational movement therebetween; and
the second coupling housing including an aperture therethrough for receiving the spherical upper portion of the second fastener, the aperture having a concave annular sidewall configured to mate with the spherically convex surface of the spherical upper portion of the second fastener to allow rotational movement therebetween;
wherein the threaded bore of the upper spherical portion of each of the first and second fasteners has a major diameter that is constant from an upper portion of the threaded bore to a lower portion of the threaded bore, and a minor diameter that tapers from a larger diameter proximate the upper portion of the threaded bore to a smaller diameter proximate the lower portion of the threaded bore; and
wherein the threaded bore of the upper spherical portion of each of the first and second fasteners includes a thread having a crest defining the minor diameter, where the crest includes a planar surface parallel to the longitudinal axis.

12. The spinal stabilization system of claim 11, further comprising:
a first set screw threadably received in the threaded bore of the upper spherical portion of the first fastener configured to exert a radially outward force on the upper spherical portion of the first fastener to prevent rotation of the upper spherical portion in the aperture of the first coupling housing; and
a second set screw threadably received in the threaded bore of the upper spherical portion of the second fastener configured to exert a radially outward force on the upper spherical portion of the second fastener to prevent rotation of the upper spherical portion in the aperture of the second coupling housing.

13. The spinal stabilization system of claim 12, wherein each of the first and second set screws includes external threading having a major diameter that is constant from an upper portion of the set screw to a lower portion of the set screw, and a minor diameter that tapers from a larger diameter proximate the upper portion of the set screw to a smaller diameter proximate the lower portion of the set screw.

* * * * *